US007749715B2

(12) United States Patent
Russo et al.

(10) Patent No.: US 7,749,715 B2
(45) Date of Patent: Jul. 6, 2010

(54) TCL-1 GENE AND PROTEIN AND RELATED METHODS AND COMPOSITIONS

(75) Inventors: Giandomenico Russo, Rome (IT); Carlo M. Croce, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 697 days.

(21) Appl. No.: 11/412,216

(22) Filed: Apr. 25, 2006

(65) Prior Publication Data
US 2006/0188924 A1 Aug. 24, 2006

Related U.S. Application Data

(62) Division of application No. 09/441,242, filed on Nov. 16, 1999, now Pat. No. 7,175,995, which is a division of application No. 08/330,272, filed on Oct. 27, 1994, now Pat. No. 5,985,598.

(51) Int. Cl.
*G01N 33/53* (2006.01)
(52) U.S. Cl. .......................... 435/7.1; 436/518; 436/536
(58) Field of Classification Search ........................ None
See application file for complete search history.

(56) References Cited

U.S. PATENT DOCUMENTS

| 4,701,409 A | 10/1987 | Croce |
| 5,015,568 A | 5/1991 | Tsujimoto et al. |
| 5,480,968 A | 1/1996 | Kraus et al. |

FOREIGN PATENT DOCUMENTS

| WO | WO 91/00364 | 1/1991 |
| WO | WO 92/19775 | 11/1992 |
| WO | WO 93/13119 | 7/1993 |
| WO | WO 93/16178 | 8/1993 |

OTHER PUBLICATIONS

Adachi, M., et al., "Variant Translocation of the *bcl*-2 Gene to Immunoglobulin λ Light Chain Gene in Chronic Lymphocytic Leukemia," *Proc. Natl. Acad. Sci. USA* 86:2771-2774 (1989).
Baer, R., et al, "Fusion of an Immunoglobulin Variable Gene and a T Cell Receptor Constant Gene in the Chromosome 14 Inversion Associated with T Cell Tumors," *Cell* 43:705-713 (1985).
Baer, R., et al., "The Breakpoint of an Inversion of Chromosome 14 in a T-cell Leukemia: Sequences Downstream of the Immunoglobulin Heavy Chain Locus are Implicated in Tumorigenesis," *Proc. Natl. Acad. Sci. USA* 84:9069-9073 (1987).
Bertness, V.L., et al., "Characterization of the Breakpoint of a t(14;14)(q11.2;q32) from the Leukemic Cells of a Patient with T-cell Acute Lymphoblastic Leukemia," *Cancer Genet. Cytogenet.* 44:47-54 (1990).
Brito-Babapulle, V., and Catovsky, D., "Inversions and Tandem Translocations Involving Chromosome 14q11 and 14q32 in T-prolymphocytic Leukemia and T-cell Leukemias in Patients with Ataxia Telangiectasia," *Cancer Genet. Cytogenet.* 55:1-9 (1991).

Buckler, A.J., et al., "Exon Amplification: a Strategy to Isolate Mammalian Genes Based on RNA Splicing," *Proc. Natl. Acad. Sci. USA* 88:4005-4009 (1991).
Croce, C.M., et al., "Transcriptional Activation of an Unrearranged and Untranslocated c-*myc* Oncogene by Translocation of a $C_\lambda$ Locus in Burkitt Lymphoma Cells," *Proc. Natl. Acad. Sci. USA* 80:6922-6926 (1983).
Croce, C.M., et al., "Gene for α-chain of Human T-cell Receptor: Location on Chromosome 14 Region Involved in T-cell Neoplasms," *Science* 277:1044-1047 (1985).
Croce, C.M., "Role of Chromosome Translocations in Human Neoplasia," *Cell* 49:155-156 (1987).
Dalla-Favera, R., et al., "Human c-*myc onc* Gene is Located on the Region of Chromosome 8 that is Translocated in Burkitt Lymphoma Cells," *Proc. Natl. Acad. Sci. USA* 79:7824-7827 (1982).
Davis, L.G., et al., "Basic Methods in Molecular Biology," Elsevier Science Publishing Co., Inc., New York, New York, pp. v-vii (1986).
Ellisen, L.W., et al., "*TAN-I*, the Human Homolog of the Drosophila Notch Gene, is Broken by Chromosomal Translocations in T Lymphoblastic Neoplasms," *Cell* 66:649-661 (1991).
Erikson, J., et al., "Translocation of an Immunoglobulin κ Locus to a Region 3' of an Unrearranged c-*myc* Oncogene Enhances c-*myc* Transcription," *Proc. Natl. Acad. Sci. USA* 80:7581-7585 (1983).
Erikson, J., et al., "Deregulation of c-*myc* by Translocation of the α-Locus of the T-Cell Receptor in T-Cell Leukemias," *Science* 232:884-886 (1986).
Haluska, F. G., et al., "Oncogene Activation by Chromosome Translocation in Human Malignancy," *Ann. Rev. Genet.* 21:321-345 (1987).
Hamaguchi, M., et al., "Establishment of a Highly Sensitive and Specific Exon-trapping System," *Proc. Natl. Acad. Sci. USA* 89:9779-9783 (1992).
Isobe, M., et al., "Cloning of the Gene Encoding the δ Subunit of the Human T-cell Receptor Reveals its Physical Organization Within the α-subunit Locus and its Involvement in Chromosome Translocations in T-cell Malignancy," *Proc. Natl. Acad. Sci. USA* 85:3933-3937 (1988).
Lindsay, S., and Bird, A. P., "Use of Restriction Enzymes to Detect Potential Gene Sequences in Mammalian DNA," *Nature* 327:336-338 (1987).
Magrath, I.T., et al., "Characterization of Lymphoma-derived Cell Lines: Comparison of Cell Lines Positive and Negative for Epstein-Barr Virus Nuclear Antigen. II. Surface Markers," *J. Natl. Cancer Inst.* 64(3):477-483 (1980).

(Continued)

*Primary Examiner*—James S Ketter
(74) *Attorney, Agent, or Firm*—Hamilton, Brook, Smith & Reynolds, P.C.

(57) ABSTRACT

The present invention relates to nucleotide sequences of TCL-1 genes and amino acid sequences of their encoded proteins, as well as derivatives and analogs thereof, and antibodies thereto. The TCL-1 gene sequence is preferentially expressed early in T and B lymphocyte differentiation. The present invention further relates to the use of TCL-1 genes and their encoded proteins as diagnostic and therapeutic reagents for the detection and treatment of disease states associated with chromosomal abnormalities.

8 Claims, 18 Drawing Sheets

OTHER PUBLICATIONS

Figure 1A:
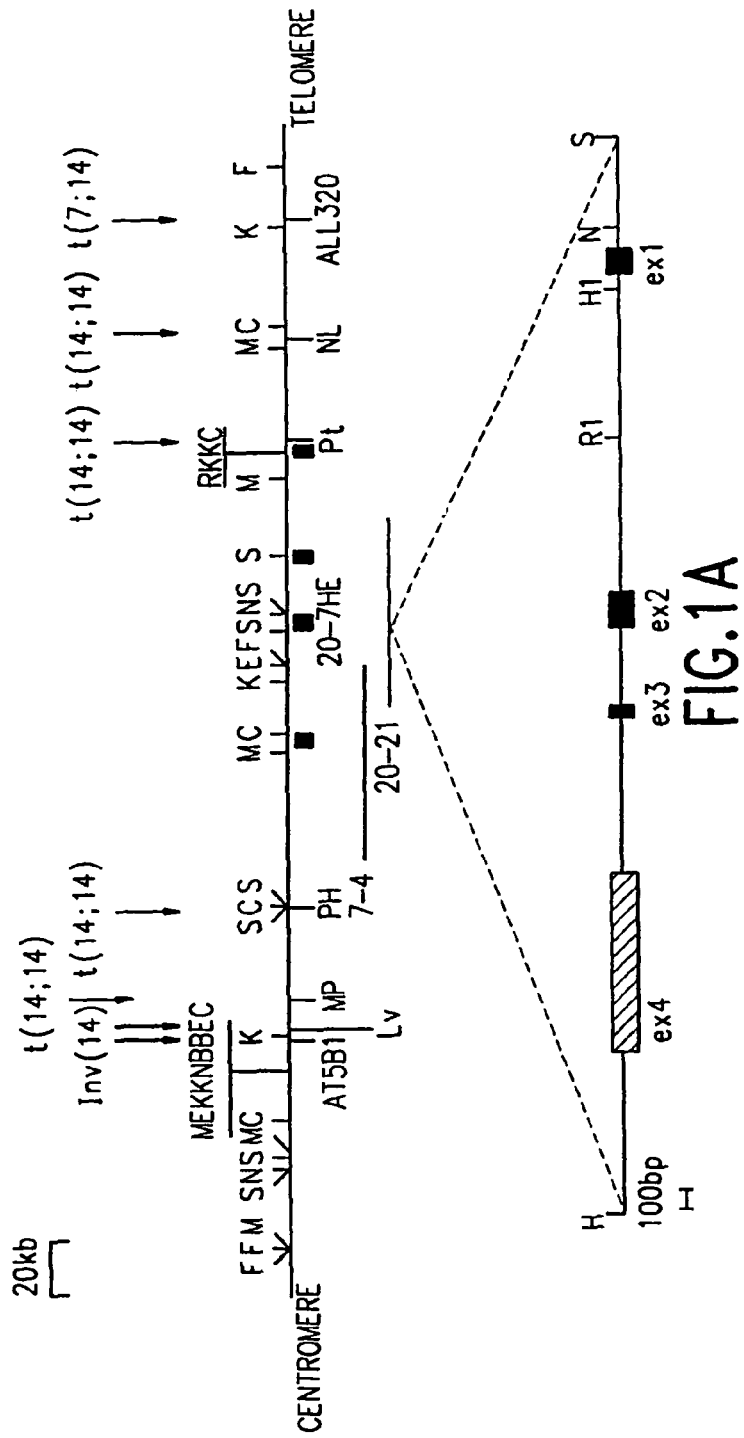

Mengle-Gaw, L., et al., "Human T-cell Tumours Containing Chromosome 14 Inversion or Translocation with Breakpoints Proximal to Immunoglobulin Joining Regions at 14q32," *EMBO J.*, 6(8):2273-2280 (1987).

Motokura, T., and Arnold, A., "*PRAD1*/Cyclin D1 Proto-oncogene: Genomic Organization, 5' DNA Sequence, and Sequence of a Tumor-specific Rearrangement Breakpoint," *Genes Chromosom. Cancer* 7:89-95 (1993).

Nishikura, K., et al., "Differential Expression of the Normal and of the Translocated Human c-*myc* Oncogenes in B Cells," *Proc. Natl. Acad. Sci. USA* 80:4822-4826 (1983).

Nishimoto, N., et al., "Normal Pre-B Cells Express a Receptor Complex of μ Heavy Chains and Surrogate Light-chain Proteins," *Proc. Natl. Acad. Sci. USA* 88:6284-6288 (1991).

Rosenberg, C. L., et al.,"*PRAD1*, a Candidate *BCL1* Oncogene: Mapping and Expression in Centrocytic Lymphoma," *Proc. Natl. Acad. Sci. USA* 88:9638-9642 (1991).

Russo, G., et al., "Molecular Analysis of a t(7;14)(q35;q32) Chromosome Translocation in a T Cell Leukemia of a Patient with Ataxia Telangiectasia," *Cell* 53:137-144 (1988).

Russo, G., et al., "Molecular Analysis of a t(14;14) Translocation in Leukemic T-Cells of an Ataxia Telangiectasia Patient," *Proc. Natl. Acad. Sci. USA* 86:602-606 (1989).

Sambrook, J., et al., Molecular Cloning, A Laboratory Manual, 2d ed., Cold Spring Harbor Laboratory Press, New York, pp. 9.31-9.57 (1989).

Smith, S.D., et al., "Long-term Growth of Malignant Thymocytes in Vitro," *Blood* 73(8):2182-2187 (1989).

Tsujimoto, Y., et al., "Molecular Cloning of the Chromosomal Breakpoint of B-cell Lymphomas and Leukemias with the t(11;14) Chromosome Translocation," *Science* 224:1403-1406 (1984).

Tsujimoto, Y., et al., "Involvement of the *bcl*-2 Gene in Human Follicular Lymphoma," *Science* 228:1440-1443 (1985).

Tsujimoto, Y., and Croce, C. M., "Analysis of the Structure, Transcripts, and Protein Products of *bcl*-2, the Gene Involved in Human Follicular Lymphoma," *Proc. Natl. Acad. Sci. USA* 83:5214-5218 (1986).

Virgilio, L., et al., "Chromosome Walking on the *TCL1* Locus Involved in T-cell Neoplasia," *Proc. Natl. Acad. Sci. USA* 90:9275-9279 (1993).

Withers, D. A., et al., "Characterization of a Candidate *bcl-1* Gene," *Mol. Cell. Biol.* 11(10):4846-4853 (1991).

Elshourbagy, N. A., et al., "Structure and Expression of the Human Apolipoprotein A-IV Gene," *J. Biol. Chem.* 262:7973-7981 (1987).

Uhlmann, E. and Peyman, A., "Antisense Oligonucleotides: A New Therapeutic Principle," *Chem. Rev.* 90(4): 543-584 (1990).

Wallace, R. B., and Miyada, C. G., "Oligonucleotide Probes for the Screening of Recombinant DNA Libraries," in *Guide to Molecular Cloning Techinques, Methods in Enzymology*, vol. 152 (S.L. Berger and A.R. Kimmel, Eds.) New York: Academic Press, 1987, pp. 432-442.

Fu, Z.-Q., et al., "Crystal Structure of MTCP-1: Implications for Role of TCL-1 and MTCP-1 in T Cell Malignancies," *Proc. Natl. Acad. Sci. USA* 95:3413-3418 (1998).

Stern, M.-H., et al., "MTCP-1: a Novel Gene on the Human Chromosome Xq28 Translocated to the T Cell Receptor α/δ Locus in Mature T Cell Proliferations,"*Oncogene* 8:2475-2483 (1993).

Hancock, D. C., et al., "Synthesis of Peptides for Use as Immunogens," in *Methods in Molecular Biology*, J.D. Pound, editor. Humana Press, 1998. vol. 80:69-79.

Wahl, G. M., et al., "Molecular Hybridization of Immobilized Nucleic Acids: Theoretical Concepts and Practical Considerations," in *Methods in Enzymology*, Berger & Kimmel, editors. Academic Press, vol. 152, pp. 399-407, (1987).

Kuby, J., *Immunology*, 2nd ed., (NY: W. H. Freeman & Co.), pp. 91-96 (1991).

```
  1    CTTGAGAGGCTCTGGCTCTTGCTTCTTAGGCGGCCCGAGGACGCCATGGCCGAGTGCCCG
                                                        M  A  E  C  P
 61    ACACTCGGGGAGGCAGTCACCGACCACCCGGACCGCCTGTGGGCCTGGGAGAAGTTCGTG
        T  L  G  E  A  V  T  D  H  P  D  R  L  W  A  W  E  K  F  V
121    TATTTGGACGAGAAGCAGCACGCCTGGCTGCCCTTAACCATCGAGATAAAGGATAGGTTA
        Y  L  D  E  K  Q  H  A  W  L  P  L  T  I  E  I  K  D  R  L
181    CAGTTACGGGTGCTCTTGCGTCGGGAAGACGTCGTCCTGGGGAGGCCTATGACCCCCACC
        Q  L  R  V  L  L  R  R  E  D  V  V  L  G  R  P  M  T  P  T
241    CAGATAGGCCCAAGCCTGCTGCCTATCATGTGGCAGCTCTACCCTGATGGACGATACCGA
        Q  I  G  P  S  L  L  P  I  M  W  Q  L  Y  P  D  G  R  Y  R
301    TCCTCAGACTCCAGTTTCTGGCGCTTAGTGTACCACATCAAGATTGACGGCGTGGAGGAC
        S  S  D  S  S  F  W  R  L  V  Y  H  I  K  I  D  G  V  E  D
361    ATGCTTCTCGAGCTGCTGCCAGATGACTGATGTATGGTCTTGGCAGCACCTGTCTCCTTT
        M  L  L  E  L  L  P  D  D  *  114
421    CACCCCAGGGCCTGAGCCTGGCCAGCCTACAATGGGGATGTTGTGTTTCTGTTCACCTTC
481    GTTTACTATGCCTGTGTCTTCTCCACCACGCTGGGGTCTGGGAGGAATGGACAGACAGAG
541    GATGAGCTCTACCCAGGGCCTGCAGGACCTGCCTGTAGCCCACTCTGCTCGCCTTAGCAC
601    TACCACTCCTGCCAAGGAGGATTCCATTTGGCAGAGCTTCTTCCAGGTGCCCAGCTATAC
661    CTGTGCCTCGGCTTTTCTCAGCTGGATGATGGTCTTCAGCCTCTTTCTGTCCCTTCTGTC
721    CCTCACAGCACTAGTATTTCATGTTGCACACCCACTCAGCTCCGTGAACTTGTGAGAACA
781    CAGCCGATTCACCTGAGCAGGACCTCTGAAACCCTGGACCAGTGGTCTCACATGGTGCTA
841    CGCCTGCATGTAAACACGCCTGCAAACGCTGCCTGCCGGTAAACACGCCTGCAAACGCTG
901    CCTGCCCGTAAACACGCCTGCAAACGCTGCCTGCCCACACAGGTTCACGTGCAGCTCAAG
961    GAAAGGCCTGAAAGGAGCCCTTATCTGTGCTCAGGACTCAGAAGCCTCTGGGTCAGTGGT
1021   CCACATCCCGGGACGCAGCAGGAGGCCAGGCCGGCGAGCCCTGTGGATGAGCCCTCAGAA
1081   CCCTTGGCTTGCCCACGTGGAAAAGGGATAGAGGTTGGGTTTCCCCCCTTTATAGATGGT
1141   CACGCACCTGGGTGTTACAAAGTTGTATGTGGCATGAATACTTTTTGTAATGATTGATTA
1201   AATGCAAGATAGTTTATCTAACTTCGTGCGCAATCAGCTTCTATCCTTGACTTAGATTCT
1261   GGTGGAGAGAAGTGAGAATAGGCAGCCCCCAAA<u>TAAAA</u>AAATATTCATGGAAAAAAAAAAA
1321   AAAA    1324
```

FIG.3A

```
  1    GTCGACTGTGAGTTCCCAGCAGAGGCCCAGAGTCCCGGTCCGGCAGCCGAGGGAAGCGGG
 61    GGGGTCTTCCAGAAGAAGAAAGGGCCAAGGTCACCCCGGTGCCTCTCCAGCAGCAGCAGA
121    GGGCGGCGGTCGGTGTCGCTGCTGGCCGGGGCCTCGAGGAAGGCGCGGGCCAGCTGGGGC
181    CGGGTCTGCGTTCCCAGGAGCTGCCACCGTTCCAGGGAGCAAGTCAGGCCGGGACGTTAG
241    CGCCTGCGCGGGACCCTCACTTGCCACCAAGGACCCCACAAACCCCGCCCCATCCTTAGC
301    GCCTGCGCGGGACCCTCACTTGCCACCAAGACCCCCACAAACCCCGCCCCATCCTGCCTT
361    ACGCCCCGCCCCAAGGTCGTTCTCCCGACCCGGGGTCCCGCCCCAAGACCGTCCTCCCGC
421    CCCGCCGCTTGGTGGCGGCCGCATGCTGCCCGGATATAAAGGGTCGGCCCCACATCCCAG
481    GGACCAGCGAGCGGCCTTGAGAGGCTCTGGCTCTTGCTTCTTAGGCGGCCCGAGGACGCC
541    ATGGCCGAGTGCCCGACACT    560
```

FIG.3B

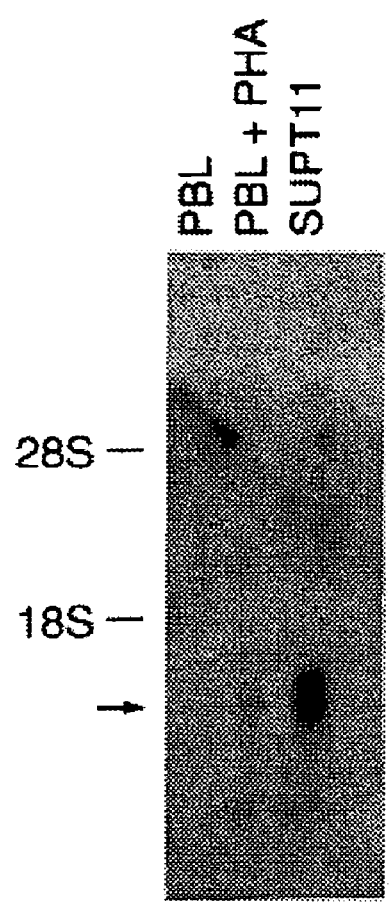
FIG.5A
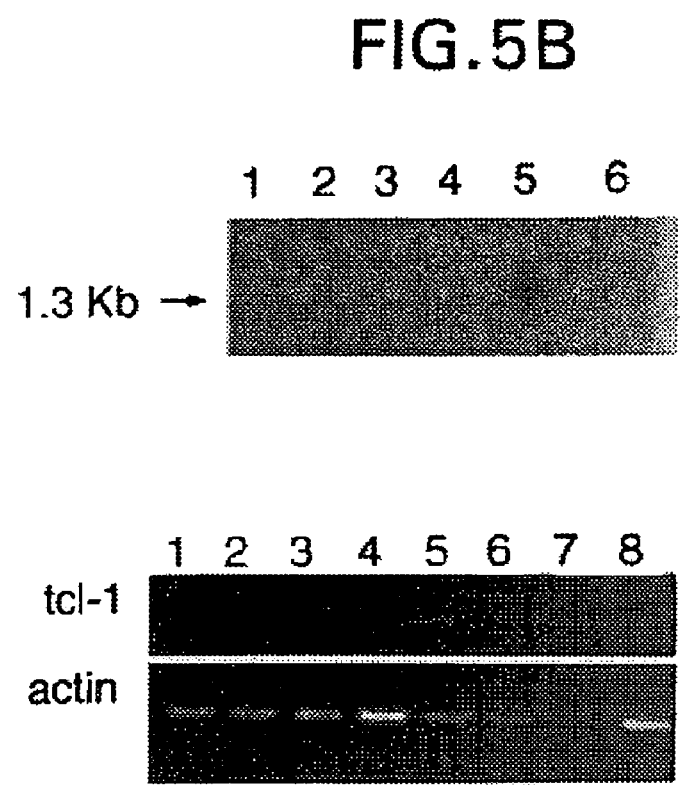
FIG.5B
FIG.5C

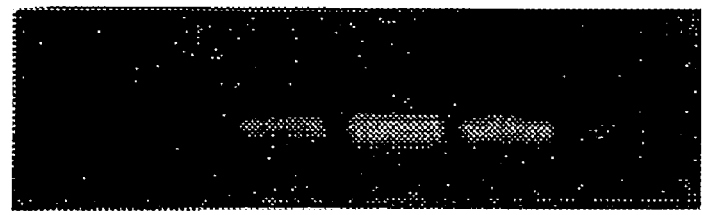
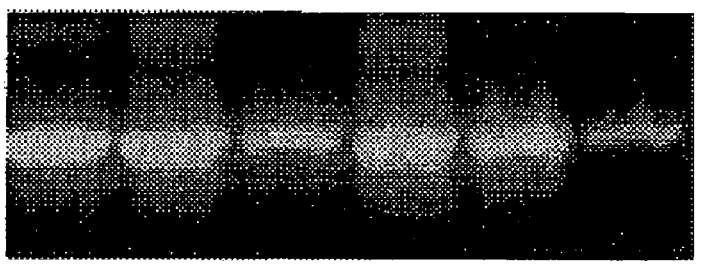
FIG. 7

```
              10        20        30        40        50        60
TCL-1   MAECPTLGEAVTDHPDRLWAWEKFVYLDEKQHAWLPLTIEIKDRLQLRVLLRREDVVLGR
             |:|:||:|||:  ::  :|  ||   |:::|| ::: :|  ||
MTCP1             MAGEDVGAPPDHLWVHQEGIYRDEYQRTWVAV-VEEETSF-LRARVQQIQVPLGD
                    10        20        30        40        50

70        80        90       100       110
TCL-1   SMTPTQIGPSLLPIMWQLYPDGRYRSSDSSFWRLVYHIKIDGVEDMLLELLPDDX
        ::  |:::  :|  |||||| ||||||| ||:::  :|::  ||::|||||||
MTCP1   AARPSHLLTSQLPLMWQLYPEERYMDNNSRLWQIQHHLMVRGVQELLKLLPDDX
              60        70        80        90       100
```

FIG.8

```
  1  GTCGACTTGT GAKTYCCMAG MAGAGGCCCA GAAGTCCCGGTCCGGCAAAG
 51  CGGAGGGGAA GCGGGGGGGG TCTTCCAAGA AGAAGAAAGGGCCCAAGGTT
101  CAACCCCCGG TGCCTTCTCC AGCAGCAAGC AAGAGGGGCGGGGGTCGGTT
151  GTCGCTGCTG GCCGGGGGCC TCCGAGGAAA GGCGCGGRCCAGCTGGGGCC
201  GGGTCTGCGT TCCCAGGAGC TGCCACCCGTT CCAGGGAGCAAGTCAGGCCG
251  GGACGTTAGC GCCTGCGCGG GACCCTCACT TGCCACCAAGRMCCCCACAA
301  ACCCCGCCCC ATCCTGYCTT ACGCCCCGCC CCAAGTCGGTTCTCCCCGA
351  CCCGGGGTC CCGCCCCCAA GGNCCGTCCT CCCCGCCCCGSTTGT
401  GGCGGCCGCA TGCTGCCCGG ATATAAAGGG TCGGCCCCACATCCCAGGGA
451  CCAGCGAGCG GCCTTGAGAG GCTCTGGCTC TTGCTTCTTAGGGGCCCGA
501  GGACGCCATG GCCGAGTGCC CGACACTCGG GGAGGCAGTCACCGACCACC
551  CGGACCGCCT GTGGGCCTGG GAGAAGTTCG TGTATTTGGACGAGAAGCAG
601  MACGCCTGCC TGCCCTTAAC CATCGAGGTA CAACCACCTTTGGAGCGGAT
651  GGCGARGCAG CAGGGGCASC CCCTGGGAGC TTGGGATNCCCTAGGAAGGG
```

FIG.9A

```
 701   CGAGGACTCA AGGAGCACTC ACTATGGGGC AGGGAGGATC CCCACAGAT
 751   KAAGCCACTT TTGGAGCCGG SCTCTKGAGG GATGAATAGG AGTTCCTCCA
 801   GGCAGGGAAG AAGGGTGGGA AAACCCCAAA GGAATGTCGG TCAAAGGGGT
 851   GGACCCAGTG CCTGTGGAGT GTGACTATAA TGTTGACTAC AGGCAGGCATT
 901   TTCTGGGCTT CGGGGTCCTA ATCCTTAAAA ATGGGTATCT CTAAGTGACT
 951   CATCCATATG GCCGATTATC GGAATCATCT CAGGTGGGTC CCAGAAATCT
1001   GTATTTTAAA AAAGAAACCCW CMACAGTTTA GGGTCCAACC CAGGCATAAC
1051   CAAAACACTG GCCTAAGAGT TGTGAAGTAT TTTCCCACCT ACCCCTGGG
1101   CTTTATTTAA GAMAACCAAA TTTAACAAGT GATGTCGTAG TATAAGCGCC
1151   GGTANTKGAA YCAATATTGA CTTTTTTAAT GTGTGATGCC TTAAGATGGG
1201   TCCTTAATCC ATGTTAAGNT TTTGTTAAAG AAATAGATAA GTCTTTTACA
1251   AGTATTTGGA TTTACTCAAT GAAAAAGAGT CANAAAATGT TCAAACTCTC
1301   TCCAAACATA CACTGAAGAA AGCATAAAAA TTANNAATAT ATTAGAACA
```

FIG.9B

```
1351  CGTATGTCCA GTAGCAAWCA MAAATTATTG AGTGTTGAYTGTGTCTCTAC
1401  AGATGGGAAA CTGAGGCACA CMAAATGTAC ATTTGTCCGAGGTAAGATTG
1451  CTAGTAGGTA ATGGGGYTGG AATTCTAGGC TCTTAACCACCACAAAATCT
1501  GCATTTTTAT TGGCATTTCA ATTTTTAAA TATGTTTTACTTAAAAT
1551  CAAGTAAAAT ACTTACTTTT TTAAAATCAA AATTTGAAGAAATAATTTGA
1601  AGATTCAGTG GATTTCTTTT TTTAAATCTC TGAGAAATCTCTCCCTYCA
1651  ACGTGACACC MAAACCMGCG AACCAGACAG TTTTTCATAAAATCATGAAA
1701  CATGCYCCMC MAAAAATAAC CCACTASCAA ACTGTGGGACAGATTTGCC
1751  TCACATCATT GAAAAGGCCA GCAWTCTTTT TCTCTCTCTTTCTTTCTTTGKT
1801  GTTTTTTTT TTCCCTGTAG AWACAGGGTC TCGCTCTGTGACCCAGGCTG
1851  GTCTYAAACT CCTGGCCTCA AGCGATCCTC CTGCCTCTGCCTTCCAAAGC
1901  ACTGGAATTA CAAGTGTGAG CCGCTGCAAC CCGCCAGAAAAAGTGTGCC
1951  TTTCATGGCC CTGTCTGGGT GGCTAGACAC GTGTGTGTGCTGGTGGTCCT
2001  GGCCCAGCCA GAGTTCCCTG AGAGGAGCAT GCATGGCCTAAGGAAGTGAG
```

FIG. 9C

```
2051  CTTCAGGGAA  CAGTGATGAC  CATCATTTCA  CACTCGGACCCCCTGCCMAA
2101  GATGGGTGGA  TGSCTGSCAG  GGAGGGATTC  CGGTKTCCTGGCCCTGGAG
2151  AANCCCTGCC  AGCGGAACC   TGAAAGTATN  CCCTGTCCTTTTCTTCTCCT
2201  NAGATAAAGG  ATAGGTTACA  GTTNNGGGTG  CTCTTGGCTCGGAAGACGT
2251  CGTCCCTGGGG AGGCCTATGA  CCCCCACCNA  GATAGGCCCAAGCCTGCTGC
2301  CTATCATGTG  GCAGCTCTAC  CCTGATGGAC  GATACCGATCCTCAGACTCC
2351  AGTTTCTGGC  GCTTAGTGTA  CCACATCAAG  GTGAGTGTCTTTCTCCAGA
2401  GGTCCATCGG  KTGATCTTGG  GTTTCCCCTC  CYCMATGTCTGSCCTTAGTG
2451  GTTTAYCTTC  CCYCCATCCC  AGTSSGCAAA  AGCATTWAAAARATGGGGGA
2501  NRTRWACMAS  TGCAGATTTC  TANAGGACTT  TACCAGAGAGAAGANAGATC
2551  CTNTGAGGTC  TCTAANAGAA  CCCTACCTCC  ACTTCCTCCCANCCACCANC
2601  TAACCGCAGG  AAGACATCTC  TGGTGGGGMM  KCACAGGCTGAAGGCTGGTG
2651  GGAGGAGGGR  CAKTCTCCAA  GASCCCCTGA  AATCCTCACACCTGGGTTCC
```

FIG. 9D

```
2701  TACCTGCTGT  TTCCAGCTAG  GGGAAGSCSC  AGGAGTGAGGAATGGAGGGA
2751  GTGGAGGGCT  CTGGCCGATC  AATGCCTTCT  CTCTCTCTGCCTCTCAGA
2801  TTGACGGCGT  GGAGGACATG  CTTCTCGAGC  TGCTGCCAGATGACTGATGT
2851  ATGGTGAGCT  CCACTGGAGC  CTGACCCCTC  TTAGTCCACAGTGGCTGTAT
2901  CAGAAAGAAA  GACCACCCCT  TCTCCATGAA  GGCAGTGCTAACCCCTCCCC
2951  GACTGCTGCC  ATCTGAGGGT  CCCTAGGGAT  GGGAGAGGCTTCCTGGAGGC
3001  ACTCATGTCT  CCCTTACCAC  TTCGGGAGCC  AAGGGCTTTGGTAGGCAGCC
3051  CCCTTTATCG  CAGCTGCTCA  TATCTATAAA  GTACTTCACAAGTTTCAGCT
3101  GGCACTTTCA  TTTTACCATT  GCTTTTTTTT  TCTTTGGGAGATGAGTCTGG
3151  CTCTGTGGCC  CAGGCTAGAG  TGTAGTGGGT  GCAATCTCAGCTCACTGAAA
3201  GCTCTGCCTC  CCGGGTTCAC  ACCATTCTCC  TGCCTCAGCCCTCGGAGTAG
3251  CTGGGACTAC  AGGCGCCCGC  CACCACACCT  GGCTAATTTTTTTTTTTW
3301  TTWTWTTTT  TAGTAGAGMC  GGGGTTTCAC  CGTGTTAGCCAGGATGGTCT
3351  CGATCCCCTG  ACCTCATGAT  CTGCCCGCCT  CGGCCTCCCAAAGTGCTGGG
```

FIG. 9E

```
3401  ATTACAGGCA  TGAGCCACCA  CGTCCGGCCT  TACCATTGCT  TTATTAAATA
3451  AGCACTGGTG  CTTGATTATA  TCAGCTGAGC  CAGATATTAG  ATACGCTATT
3501  GAGTTTTGRG  GAAATAAGAG  TACCAAAACT  CAGAAATGAG  TTGAAGTATA
3551  GTGACATCTT  CAGATTACAG  ACCCAGGTGT  CAGAATTTGC  CTTGGCTCAG
3601  AAGGCCTCTG  GGGGCCATCC  CTGACCACTA  GGCTTCCCAC  TTAGACCTGC
3651  TCCAGCAGCA  CCACCCCTCG  SCACTGCCTG  GTCCTTTCCT  TCACCCTTGA
3701  TTCTGTCTTC  TTTGTCCTT   CTCCAGGTCT  TGGYAGCACC  TGTCTCCTTT
3751  CACCCCAGGG  CCTGAGCCTG  GCCAGCCTAC  AATGGGGATG  TTGTGTTTCT
3801  GTTCACCTTC  GTTTACTATG  BCTGTGTCTT  CTCCACCGCT  GGGGTCTG
3851  GGAGGAATGG  ACAGACAGAG  GATGAGCTCT  ACCCRGGGCC  TGSAGGACCT
3901  GTCCTGTAGM  CCACTCTGCT  CGCCTTAGSA  CCTACSACTC  CWRCCGASGA
3951  GGATNCCANT  TGGAAGAGCT  TCTTNNAGGT  GNCNAANANA  NCTGTGCGT
4001  NGGCTTTCT   CAGCTGGATG  ATGGTCNTNA  GCCTCTTTCT  GTCCCTTCTG
```

FIG. 9F

```
4051  TCCCTCACAG  CACTAGTATT  TNATGTTGCA  CACCCACTCAGCTCCGTGAA
4101  TTTGTGAGAA  CACAACCGAT  TCACCTGAGC  AGGACCTCTGAAACCCTGGA
4151  CCAGTGGTCT  CACATGGTGC  TACGCCTGCA  TGTAAACACGCCTNCAAACG
4201  CTGCCTGCCK  GTRAACACGM  SKSYRMACAG  STGMSWRCCCGTAAACACGC
4251  CTGCAAACGC  TGCCTGCCCA  CACAGGTTCA  CGTGCAGCTCAAGGAAAGRM
4301  CTGAAARRAG  CCCTTATCTG  TGCTCAGGAC  TCAGAAGCCTCTGGGTCAGT
4351  GGTCCACATC  CCGGGACGCA  GNAGGAGGCC  AGGCCGGCGAGCCCTGTGGA
4401  TGAGCCCTCA  GAACCCTTGG  GTTGCCCACG  TGGAAAGGGATAGAGGTTG
4451  GGTTTCCCCC  CTTTTATAGA  TGGTCACGCA  CCTGGGTGTTACAAAGTTGT
4501  ATGTGGCATG  AATACTTGNT  GTNATGATTG  ATTAAATGCAAGATAGTTTA
4551  TCTAACTTCG  TGCGGAATCA  GCTTCTATCC  TTGNCTTAGATTCTGGTGGA
4601  GAGAAGTGAN  AATAGGCAGN  CCCCANATAA  ANAATATTCANGGGATTTAT
4651  TTTATTNTTC  CTTTTGGGNG  ATNNGGGACT  ACATTNTNCNNCCCGTNTA
4701  ATCCAATGNT  TAAANCCCCA  GTGTTCTTGG  AGGNCNTACGTCGAANACCA
```

FIG. 9G

```
4751    TTGGNGTANG  CAACCTCAAA  ATTTTTNNGT  TGNNAATTNCCNGTTTTCCA
4801    GAGNCCCCCC  CNTNCTCCAT  CTTNNTCCTN  GCCCNCCCTNNCCTCCCNCA
4851    NTCCCNANGT  TNCCCTCGNC  CCCAGTCAGT  TCTTTCTCCNNCTTTANCCG
4901    NTNATNTCAC  CAGNTTCTTT  CT
```

FIG. 9H

US 7,749,715 B2

TCL-1 GENE AND PROTEIN AND RELATED METHODS AND COMPOSITIONS

RELATED APPLICATIONS

This application is a divisional of U.S. application Ser. No. 09/441,242, filed Nov. 16, 1999, now U.S. Pat. No. 7,175,995 which is a divisional of U.S. application Ser. No. 08/330,272, filed on Oct. 27, 1994 (now issued as U.S. Pat. No. 5,985, 598). The entire teachings of both applications are incorporated herein by reference.

This invention was made in part with government support under Grant number CA 39860 awarded by the National Institutes of Health. The government has certain rights in the invention.

1. INTRODUCTION

The present invention relates to nucleotide sequences of TCL-1 genes and amino acid sequences of their encoded proteins, as well as derivatives and analogs thereof and antibodies thereto. The present invention relates to the use of nucleotide sequences of TCL-1 genes and amino acid sequences of their encoded proteins, as well as derivatives and analogs thereof and antibodies thereto, as diagnostic and therapeutic reagents for the detection and treatment of disease states associated with chromosomal abnormalities. The present invention also relates to therapeutic compositions comprising TCL-1 proteins, derivatives or analogs thereof, antibodies thereto, nucleic acids encoding the TCL-1 proteins, derivatives or analogs, and TCL-1 antisense nucleic acid.

2. BACKGROUND OF THE INVENTION

There is a close association between particular chromosomal abnormalities, e.g., chromosomal translocations, inversions, and deletions, and certain types of malignancy indicating that such abnormalities may have a causative role in the cancer process. Chromosomal abnormalities may lead to gene fusion resulting in chimeric oncoproteins, such as is observed in the majority of the tumors involving the myeloid lineage. Alternatively, chromosomal abnormalities may lead to deregulation of protooncogenes by their juxtaposition to a regulatory element active in the hematopoietic cells, such as is observed in the translocation occurring in the lymphocytic lineage (Virgilio et al., 1993, Proc. Natl. Acad. Sci. USA 90:9275-9279).

Non random chromosomal translocations are characteristic of most human hematopoietic malignancies (Haluska et al., 1987, Ann. Rev. Genet. 21:321-345) and may be involved in some solid tumors (Croce, 1987, Cell 49:155-156). In B and T cells, chromosomal translocations and inversions often occur as a consequence of mistakes during the normal process of recombination of the genes for immunoglobulins (Ig) or T-cell receptors (TCR). These rearrangements juxtapose enhancer elements of the Ig or TCR genes to oncogenes whose expression is then deregulated (Croce, 1987, Cell 49:155-156). In the majority of the cases, the rearrangements observed in lymphoid malignancies occur between two different chromosomes.

The TCL-1 locus on chromosome 14 band q32.1 is frequently involved in the chromosomal translocations and inversions with the T-cell receptor genes observed in several post-thymic types of T-cell leukemias and lymphomas, including T-prolymphocytic leukemias (T-PLL) (Brito-Babapulle and Catovsky, 1991, Cancer Genet. Cytogenet. 55:1-9), acute and chronic leukemias associated with the immunodeficiency syndrome ataxia-telangiectasia (AT) (Russo et al., 1988, Cell 53:137-144; Russo et al., 1989, Proc. Natl. Acad. Sci. USA 86:602-606), and adult T-cell leukemia (Virgilio et al., 1993, Proc. Natl. Acad. Sci. USA 90:9275-9279).

Rearrangements of the TCL-1 locus at chromosome 14q32.1 are unique, in that the other locus involved in these rearrangements, namely the TCR α/δ locus, is also on chromosome 14 at subband q11 (Croce et al., 1985, Science 227: 1044-1047; Isobe et al., 1988, Proc. Natl. Acad. Sci. USA 85:3933-3937). For this reason, the rearrangements observed cytogenetically are either chromosomal inversions, inv(14) (q11;q32), involving only one of the chromosomes 14 or translocations involving both chromosomes 14 such as the t(14;14) (q11;q32), or more rarely, the t(7;14) (q35;q32) involving the TCR β locus at 7q35 (Isobe et al., 1988, Proc. Natl. Acad. Sci. USA 85:3933-3937). Several of the breakpoints at 14g32.1 involved in these translocations have been cloned and characterized (Russo et al., 1988, Cell 53:137-144; Baer et al., 1987, Proc. Natl. Acad. Sci. USA 84:9069-9073; Mengle-Gaw et al., 1987, EMBO J. 6:2273-2280; Bertness et al., 1990, Cancer Genet. Cytogenet. 44:47-54).

The TCL-1 locus, a chromosomal region of approximately 350 kb as determined by placement of translocation breakpoints on the long range genomic map, has recently been cloned (Virgilio et al., 1993, Proc. Natl. Acad. Sci. USA 90:9275-9279). The involvement of such a large region in translocation events suggests that activation of the putative TCL-1 gene may occur from a distance of many kilobases, as previously observed for the BCL-1/CCND1 gene in mantle cell lymphoma (Tsujimoto et al., 1984, Science 224:1403-1406; Rosenberg et al., 1991, Proc. Natl. Acad. Sci. USA 88:9638-9642; Withers et al., 1991, Mol. Cell. Biol. 11:4846-4853; Motokura and Arnold, 1993, Genes, Chrom. & Cancer 7:89-95) and the MYC oncogene in Burkitt lymphoma (Dalla-Favera et al., 1982, Proc. Natl. Acad. Sci. USA 79:7824-7827; Nishikura et al., 1983, Proc. Natl. Acad. Sci. USA 80:4822-4826) and in acute T-cell leukemia (Erikson et al., 1986, Science 232:884-886).

There remains an unfulfilled need to isolate and characterize the TCL-1 gene associated with chromosomal abnormalities, e.g., chromosomal translocations, inversions and deletions, for use as a diagnostic and therapeutic/prophylactic reagent in the detection, treatment, and prevention of diseases, such as T-cell leukemias and lymphomas, associated with such chromosomal abnormalities.

Citation of references hereinabove shall not be construed as an admission that such references are prior art to the present invention.

3. SUMMARY OF THE INVENTION

The present invention relates to nucleotide sequences of TCL-1 genes, and amino acid sequences of their encoded TCL-1 proteins, as well as derivatives and analogs thereof, and antibodies thereto. The present invention further relates to nucleic acids hybridizable to or complementary to the foregoing nucleotide sequences as well as equivalent nucleic acid sequences encoding a TCL-1 protein.

The present invention also relates to expression vectors encoding a TCL-1 protein, derivative or analog thereof, as well as host cells containing the expression vectors encoding the TCL-1 protein, derivative or analog thereof. As used herein, "TCL-1" shall be used with reference to the TCL-1 gene, whereas "TCL-1" shall be used with reference to the protein product of the TCL-1 gene.

The present invention further relates to the use of nucleotide sequences of TCL-1 genes and amino acid sequences of their encoded TCL-1 proteins as diagnostic reagents or in the preparation of diagnostic agents useful in the detection of disease states, such as T-cell leukemias, associated with chromosomal abnormalities, in particular at 14q32.1, and/or increased levels of expression of the TCL-1 protein. The invention further -relates to the use of nucleotide sequences of TCL-1 genes and amino acid sequences of their encoded TCL-1 proteins as therapeutic/prophylactic agents in the treatment/prevention of disease states, such as T-cell leukemias, associated with chromosomal abnormalities, in particular at 14q32.1, and/or increased levels of expression of the TCL-1 protein.

The present invention provides a novel TCL-1 gene sequence that is preferentially expressed early in T and B lymphocyte differentiation pathways. The TCL-1 gene resides in a region of approximately 160 kb between two clusters of breakpoints on the TCL-1 locus, clusters of inversions on the centromeric side and clusters of simple balanced translocations on the telomeric side. As described herein, the TCL-1 gene codes for a 1.3 kb transcript that is expressed only in restricted subsets of cells within the lymphoid lineage and expressed at high levels in leukemic cells carrying a t(14:14)(q11;q32) chromosome translocation or a inv(14) (q11;q32) chromosome inversion.

The TCL-1 gene and protein sequences disclosed herein, and antibodies thereto, may be used in assays to diagnose T-cell leukemias and lymphomas associated with chromosomal abnormalities, and/or increased expression of TCL-1 protein, such as T-prolymphocytic leukemias (T-PLL), acute and chronic leukemias associated with ataxia-telangiectasia (AT), and adult T-cell leukemia, by detecting or measuring TCL-1 mRNA in or from a patient sample or by detecting or measuring levels of TCL-1 protein from a patient sample. For example, a TCL-1 sequence may be used in a Northern blot hybridization assay of RNA from biopsied or autopsied cells or tissues to diagnose disease.

The TCL-1 protein, or derivatives or analogs thereof, disclosed herein, may be used for the production of anti-TCL-1 antibodies which antibodies may be useful diagnostically in immunoassays for the detection or measurement of TCL-1 protein in a patient sample. Anti-TCL-1 antibodies may be used, for example, for the diagnostic detection or measurement of TCL-1 protein in biopsied cells and tissues.

Also disclosed herein are methods of treatment of diseases or conditions associated with chromosomal abnormalities and/or increased expression of TCL-1 proteins. Abnormalities of chromosome 14, such as inversions and translocations, particularly at 14q32.1, are associated with T-cell leukemias and lymphomas. TCL-1 gene sequences and their protein products may be used therapeutically in the treatment of disease states associated with chromosome 14 abnormalities. Anti-TCL-1 antibodies may be used therapeutically, for example, in neutralizing the activity of an overexpressed TCL-1 protein associated with disease.

Oligonucleotide sequences, including antisense RNA and DNA molecules and ribozymes, designed to inhibit the transcription or translation of TCL-1 mRNA, may be used therapeutically in the treatment of disease states associated with increased expression of TCL-1.

Proteins, peptides and organic molecules capable of modulating activity of TCL-1 may be used therapeutically in the treatment of disease states associated with aberrant expression of TCL-1.

The present invention also relates to therapeutic compositions comprising TCL-1 proteins, derivatives or analogs thereof, antibodies thereto, nucleic acids encoding the TCL-1 proteins, derivatives or analogs, and TCL-1 antisense nucleic acid.

The present invention also relates to methods of production of the TCL-1 proteins, derivatives and analogs, such as, for example, by recombinant means.

In particular embodiments of the invention described by way of Examples 6 and 7 herein, a human TCL-1 sequence is disclosed and shown to be specifically over-expressed in various T-cell malignancies.

4. DESCRIPTION OF THE FIGURES

Figure 1B:
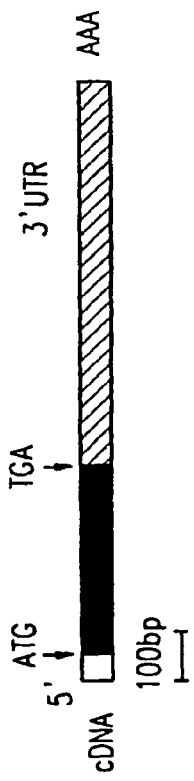

FIGS. 1A AND 1B: Genomic and cDNA organization of the TCL-1 gene 1A. Genomic organization of the TCL-1 locus on chromosome 14q32.1. Vertical bars refers to cloned breakpoints in the literature (see Virgilio et al., 1993, *Proc. Natl. Acad. Sci. USA* 90:9275-9279). Restriction sites are given for BssH II (B), Cla I (C), Eag I (E), Sfi (F), Ksp I (K), Mlu I (M), Not I (N), Nru I (R), Ecor I (R1), Sal I(S), Hind III (H) and BamH I (H1). P1 clones 7-4 and 20-21, covering the 140 kb region between the two clusters of cloned breakpoints, are shown by horizontal bars. Filled boxes represent probes used for RNA screening. Enlarged is shown a SalI-HindIII genomic fragment with the organization of the four exons of the TCL-1 gene. 1B. TCL-1 cDNA structure, open box represents 5' untranslated region, filled box represent encoding sequence and the 3' untranslated region (UTR) is shown in diagonal stripes.

Figure 2:
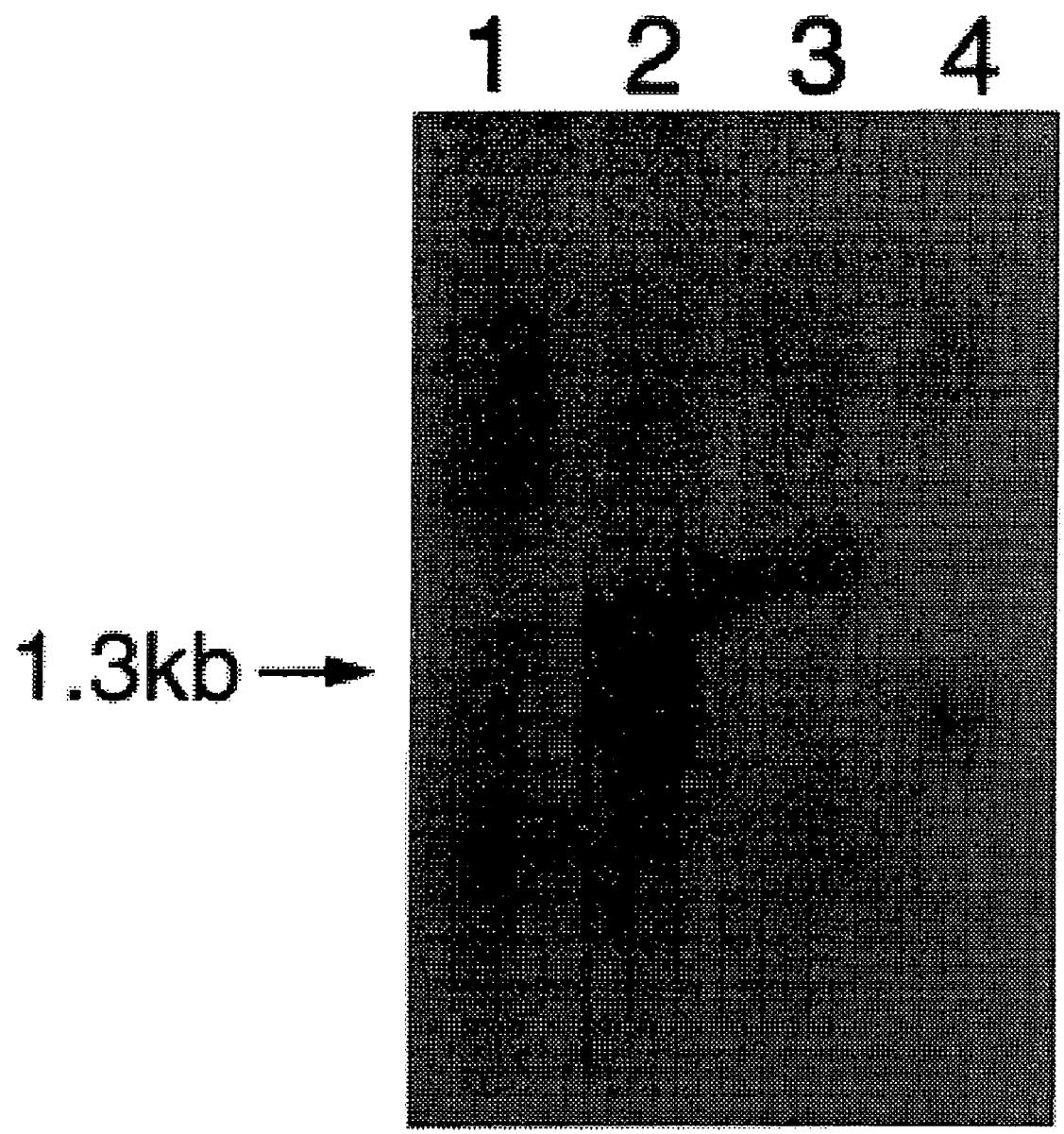

FIG. 2: Northern blot hybridization with probe 20-7HE. In each lane were loaded 11 mg of total RNA from the cell lines: Hela, lane 1; lane 2, Daudi; lane 3, K562; and lane 4, A11380.

FIGS. 3A AND 3B: cDNA sequence and 5' genomic sequence of TCL-1 3A. cDNA sequence (SEQ ID NO: 1) and encoded amino acid sequence (SEQ ID NO: 2) of TCL-1. The initiation codon ATG is shown in bold, the polyadenylation signal is underlined. 3B. Genomic sequence (SEQ ID NO: 3) 5' to the cDNA. In boxes are shown SP1 binding sites, in bold the TATA box and the start codon, and in italics, nucleotide numbers 497-560, the cDNA sequences (exon 1).

Figure 4:
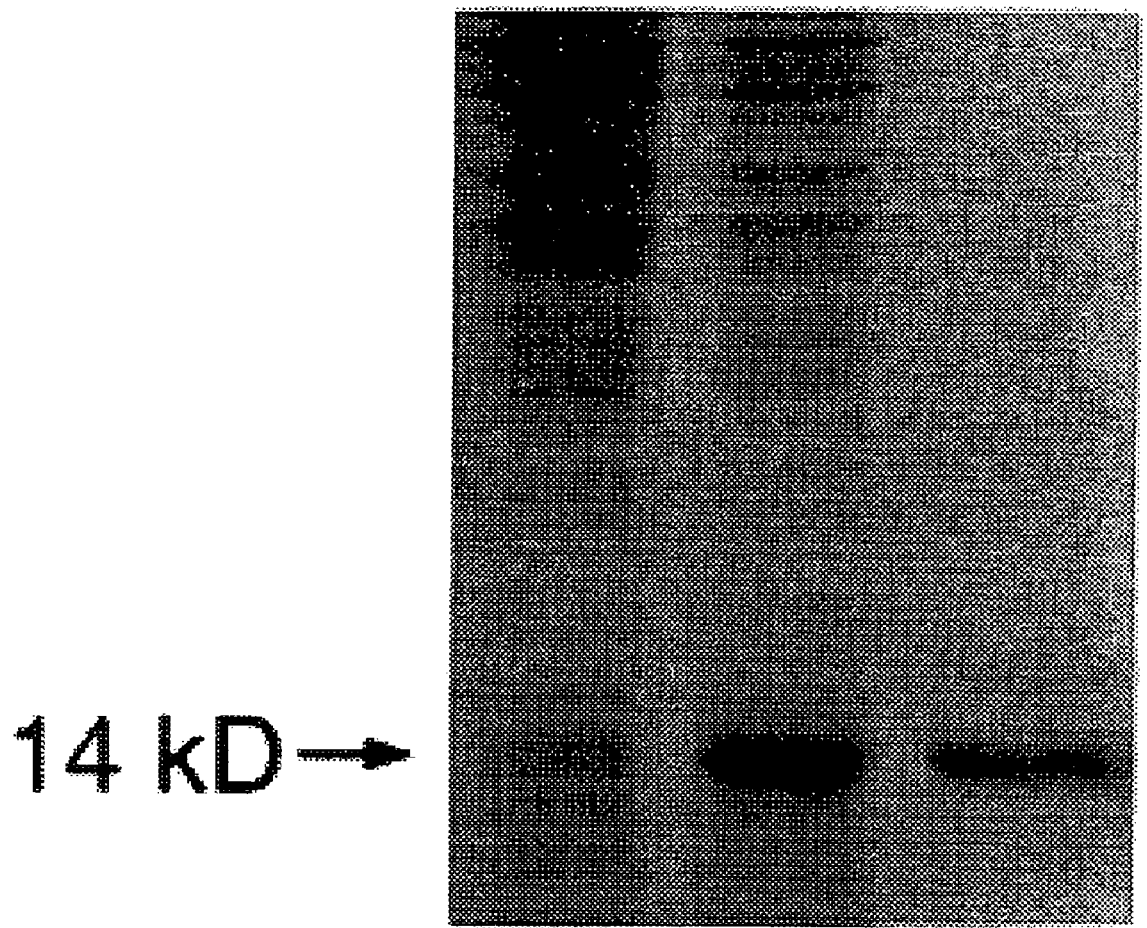

FIG. 4: Prokaryotic expression of the TCL-1 gene product. Sodium dodecyl sulfate polyacrylamide gel electrophoresis (SDS-PAGE) of bacterial lysates with pQEtcl-1, lane 1, uninduced; lane 2, induced, and lane 3, purified.

FIGS. 5A-5C: Expression of TCL-1 in different T-cells. 5A. Northern blot hybridization of stimulated and non stimulated peripheral blood lymphocytes (PBL) with a TCL-1 probe, p697; 11 mg RNA were loaded per lane. 5B. Northern blot of RNA from T-cell lines: lane 1, CEM; lane 2, Molt4; lane 3, HUT78; lane 4, SupT1; lane 5, SupT11; lane 6, Jurkat. 5C. RT-PCR with TCL-1 primers, p9A and RevIII, and with actin specific primers, Actin1 and Actin2. Lane 1, CEM cells; lane 2, HUT78 cells; lane 3, Molt4 cells; lane 4, SupT1 cells; lane 5, SupT11 cells; lane 6, PBL; lane 7, PHA activated PBL; and lane 8, fetal thymus.

Figure 6:
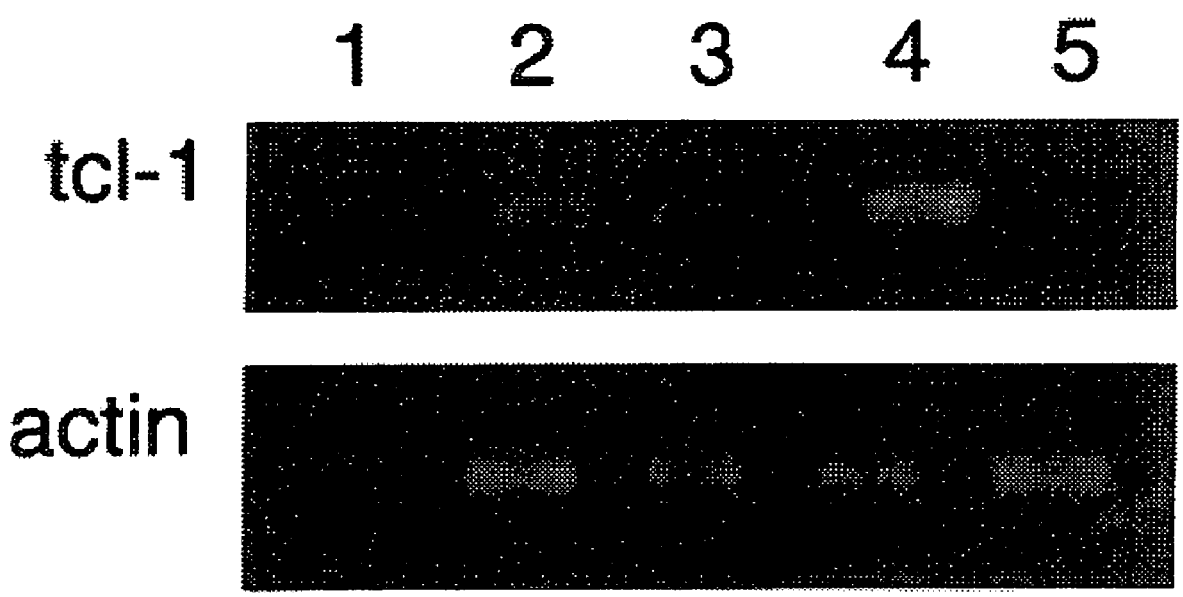

FIG. 6: Expression of TCL-1 in two patients with T-PLL. RNA isolated from patient leukemias, approximately 5 ng, were used for cDNA synthesis, followed by amplification with TCL-1 primers, Daudi unil and Daudi rev2. Lane 1, Daudi; lane 2, SupT11; lane 3, patient 312; lane 4, patient 62; and lane 5, Jurkat.

FIG. 7: Expression of TCL-1 in isolated subpopulation of bone marrow B-cells by RT-PCR. Lane 1, CD34+CD19– cells; lane 2, CD34+CD19+ cells; lane 3, CD19lom– cells; lane 4, CD19him– cells; lane 5, CD19+mlow cells, and lane 6, CD19+mhi cells.

FIG. 8: Shared sequence homology between TCL-1 protein (SEQ ID NO: 8) and Mature T-Cell Proliferative 1 (MTCP1) protein (SEQ ID NO: 4).

FIGS. 9A-9H: TCL-1 Genomic DNA sequence (SEQ ID NO: 5) between the SalI and HindIII restriction endonucleas sites (the HindIII site is not illustrated). Nucleotide numbers 422-426 represent the TATA box, nucleotide numbers 462-627 represent EXON I, nucleotide numbers 628-2203 represent INTRON I, nucleotide numbers 2204-2380 represent EXON II, nucleotide numbers 2381-2799 represent INTRON II, nucleotide numbers 2800-2853 represent EXON III, nucleotide numbers 2854-3726 represent INTRON III, and nucleotide numbers 3727-4643 represent EXON IV and 3'UT. In this genomic sequence, A represents adenine; C represents cytosine; G represents guanine; T represents thymine; U represents uracil; M represents adenine or cytosine; R represents adenine or guanine; W represents adenine or thymine/uracil; S represents cytosine or guanine; Y represents cytosine or thymine/uracil; K represents guanine or thymine/uracil; V represents adenine or cytosine or guanine, not thymine/uracil; H represents adenine or cytosine or thymine/uracil, not guanine; D represents adenine or guanine or thymine/uracil, not cytosine; B represents cytosine or guanine or thymine/uracil, not adenine; N represents (adenine or cytosine or guanine or thymine/uracil) or (unknown or other).

Figure 10:
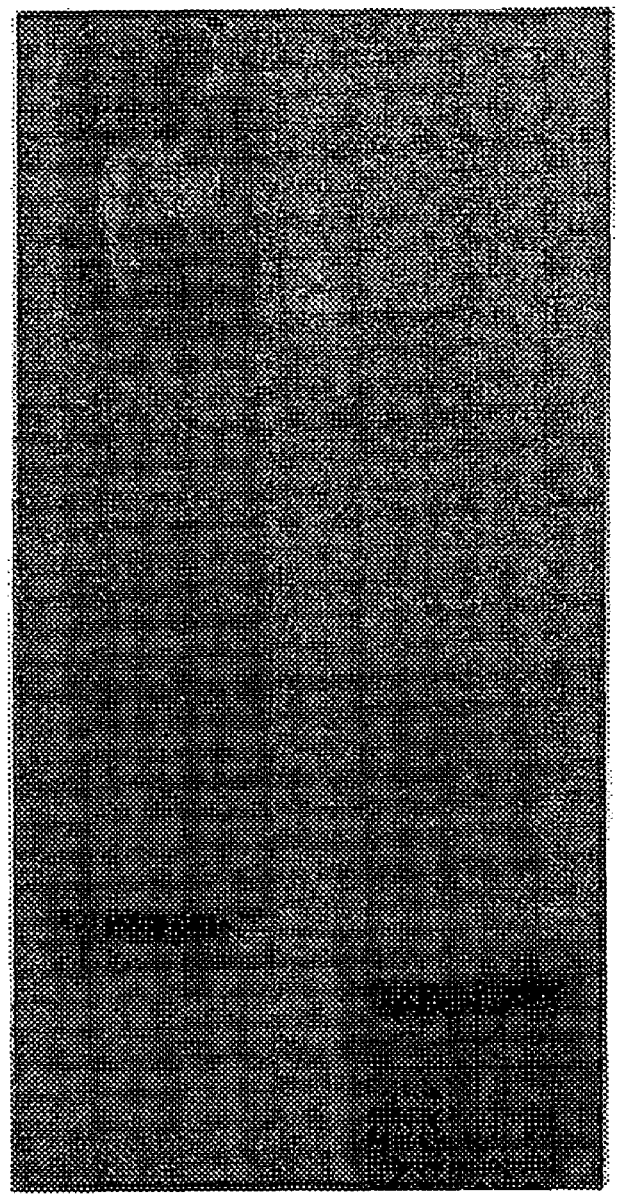

FIG. 10: In vitro translation of TCL-1 protein. Lane 1 represents the internal positive control of the kit for the Luciferase gene according to the manufacturer (Promega). Lane 2 represents the in vitro translated pAl1.5 linearized plasmid containing the TCL-1 gene.

Figure 11:
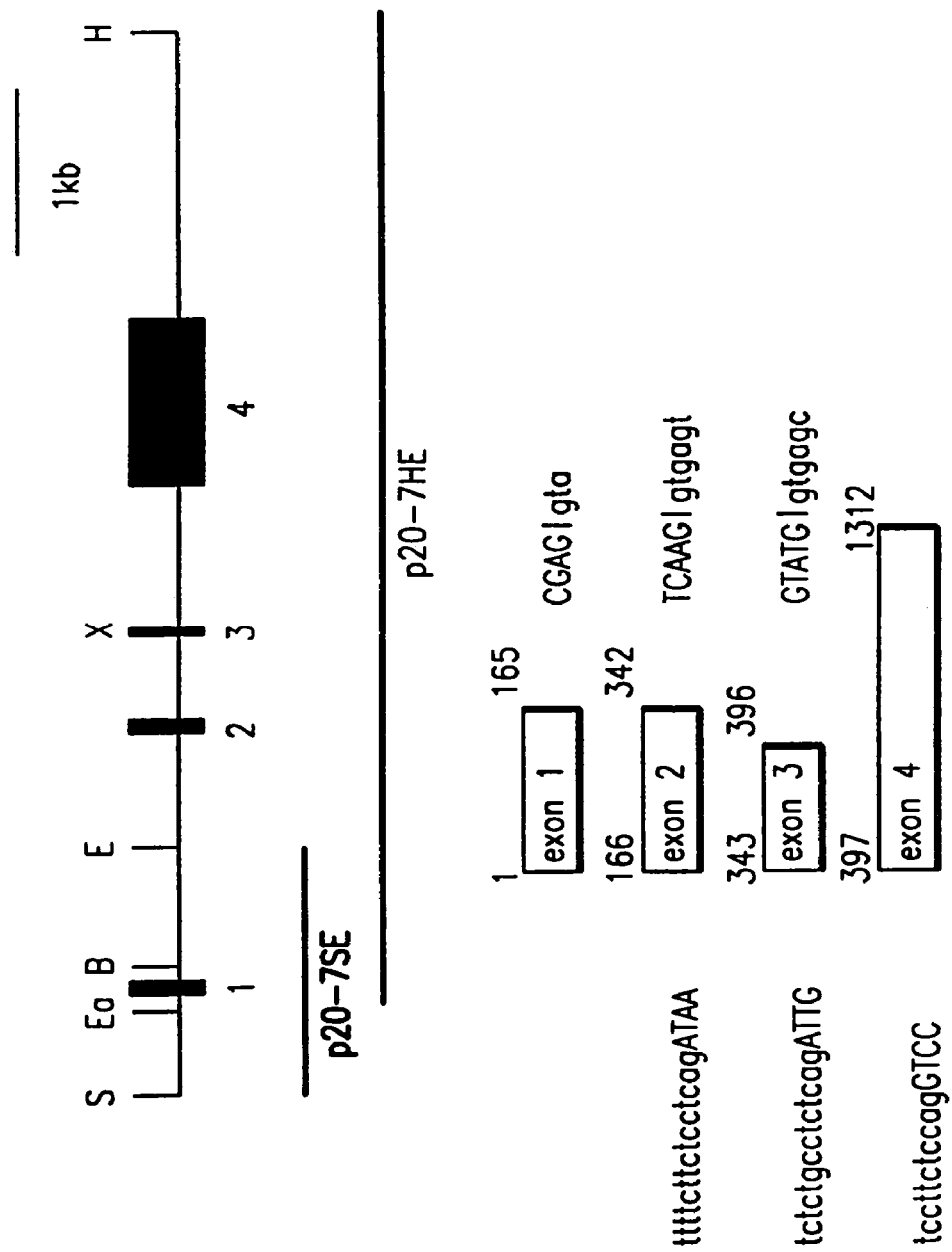

FIG. 11: Genomic organization of TCL-1 gene. The boxes represent exons. Restriction enzymes are indicated as: S=SalI, Ea=EagI, X=XhoI, H=HindIII. In the lower part are represented sequence boundaries at 3' and 5' splicing signals (lowercase). (SEQ ID NO:5, positions 2189-2207, 2376-2386, 2776-2793, 2849-2859 and 3716-3730.).

5. DETAILED DESCRIPTION OF THE INVENTION

The present invention relates to nucleotide sequences of TCL-1 genes and amino acid sequences of their encoded TCL-1 proteins, as well as derivatives and analogs thereof, and antibodies thereto.

The present invention further relates to the use of TCL-1 genes and their encoded proteins or derivatives or analogs thereof, and antibodies thereto, in assays for the detection and in treatment/prevention of disease states associated with chromosomal abnormalities and/or increased expression of TCL-1. The present invention also relates to therapeutic compositions comprising TCL-1 proteins, derivatives or analogs thereof, antibodies thereto, nucleic acids encoding the TCL-1 proteins, derivatives or analogs, and TCL-1 antisense nucleic acid.

The TCL-1 gene sequence can be from one of many different species, including but not limited to, mammalian, bovine, ovine, porcine, equine, rodent and human, in naturally occurring-sequence or in variant form, or from any source, whether natural, synthetic, or recombinant. In a specific embodiment described herein, the TCL-1 gene sequence is a human sequence. The TCL-1 protein can be that present in one of many different species, including but not limited to, mammalian, bovine, ovine, porcine, equine, rodent and human, in naturally occurring or variant form, or from any source, whether natural, synthetic, or recombinant. In specific embodiment described herein, the TCL-1 protein is a human protein.

As defined herein, a TCL-1 derivative may be a fragment or amino acid variant of the TCL-1 sequence shown in FIG. 3A as long as the fragment or amino acid variant is capable of displaying one or more biological activities associated with a full-length TCL-1 protein. Such biological activities include but are not limited to antigenicity, i.e., the ability to bind to an anti-TCL-1 antibody, and immunogenicity, i.e., the ability to generate an antibody which is capable of binding a TCL-1 protein. The invention provides fragments of a TCL-1 protein consisting of at least 10 amino acids, or of at least 25 amino acids, or of at least 50 amino acids, or of at least 114 amino acids. Nucleic acids encoding such derivatives or analogs are also within the scope of the invention. A preferred TCL-1 protein variant is one sharing at least 70% amino acid sequence homology, a particularly preferred TCL-1 protein variant is one sharing at least 80% amino acid sequence homology and another particularly preferred TCL-1 protein variant is one sharing at least 90% amino acid sequence homology to the naturally occurring TCL-1 protein over at least 25, at least 50, at least 75 or at least 100 contiguous amino acids of the TCL-1 amino acid sequence. As used herein, amino acid sequence homology refers to amino acid sequences having identical amino acid residues or amino acid sequences containing conservative changes in amino acid residues. In another embodiment, a TCL-1 homologous protein is one that shares the foregoing percentages of sequences indentical with the naturally occurring TCL-1 protein over the recited lengths of amino acids.

TCL-1 is a gene located in the region of chromosome 14q32.1 that is located in a region banded by two clusters of breakpoints. As is shown infra in Section 7, TCL-1 is preferentially expressed early in both the T and B lymphocyte differentiation pathways. As demonstrated infra in Section 7, high expression levels of TCL-1 are shown to occur in independent cases of T-PLL carrying an inversion of chromosome 14. Accordingly, the detection of TCL-1 mRNA in patient samples such as biopsied cells and tissues can be used as an indicator of the presence of T-cell leukemias and lymphomas associated with certain chromosome 14 abnormalities and/or increased expression of TCL-1 protein. Also, the TCL-1 amino acid sequences of the-present invention can be used to generate antibodies useful in immunoassays for the detection or measurement of TCL-1 in patient samples. Such anti-TCL-1 antibodies can be used in diagnostic immunoassays, for the detection or measurement of increased levels of TCL-1 associated with T-cell leukemias and lymphomas.

The present invention is illustrated infra, in part, by way of examples disclosing the cloning and sequencing of human TCL-1 and its increased expression in various T-cell malignancies.

5.1. The TCL-1 Coding Sequences

TCL-1 cDNA, genomic sequences and sequences complementary thereto are provided by the present invention. In a specific embodiment herein, a TCL-1 cDNA sequence is provided, thus lacking any introns. Also included within the scope of the present invention are polynucleotide sequences of TCL-1 cDNA consisting of at least 8 nucleotides, at least 15 nucleotides, at least 25 nucleotides, at least 50 nucleotides, at least 100 nucleotides, at least 200 nucleotides, at least 387 nucleotides, or at least 1324 nucleotides. In a specific embodiment herein, a TCL-1 genomic sequence is provided, thus containing introns. Also included within the scope of the present invention are polynucleotides of TCL-1 genomic DNA consisting of not more than 5 kilobases, of not more than 10 kilobases, not more than 25 kilobases, not more than 50 kilobases, or not more than 70 kilobases.

The full length cDNA sequence for human TCL-1 is depicted in FIG. 3A (SEQ ID NO: 1). FIG. 3B (SEQ ID NO: 3) depicts a 5' genomic (noncoding) sequence of a human TCL-1 gene from nucleotide numbers 1-496. FIGS. 9A-9D (SEQ ID NO: 5) depicts the entire genomic sequence of the TCL-1 gene. Sequence analysis of the TCL-1 cDNA of FIG. 3A reveals an open reading frame of 342 nucleotides with a starting ATG codon at position 46, located within a Kozak consensus sequence, and with a stop codon at position 388, potentially encoding a protein of 114 amino acids with a predicted molecular weight of 13.5 kDa. This sequence when subcloned in a procaryotic expression vector encodes a 14 kDa protein, that contains a casein kinase II phosphorylation site (MAECPTLGEAVTDH) (a portion of SEQ ID NO: 2) starting at amino acid position 6. As disclosed infra, see Section 6.2.3, a rabbit polyclonal anti-TCL-1 antibody has been generated that is able to immunoprecipitate naturally occurring TCL-1 protein from lymphoid and leukemia cells expressing TCL-1 mRNA confirming that the open reading frame starting with the ATG at position 46 is able to translate naturally occurring TCL-1 protein.

In accordance with the present invention, any polynucleotide sequence which encodes the amino acid sequence of a TCL-1 gene product can be used to generate recombinant molecules which direct the expression of TCL-1. Included within the scope of the present invention are polynucleotide sequences of TCL-1 consisting of at least 8 nucleotides that are useful as probes or primers (i.e., a hybridizable portion) in the detection of TCL-1. In a particular embodiment of the present invention, TCL-1 primers p9A-TGCTGCCAGAT-GACTGATGT (SEQ ID NO:6) and Rev III CAAATG-GAATCCTCCTTGGC (SEQ ID NO:7) were used to amplify TCL-1 nucleic acid from bone marrow B-cells, T-cells lines, peripheral blood lymphocytes (PBL), PHA stimulated PBL and thymus cells. In another embodiment of the present invention, amplification of DNA from patients with T-PLL was carried out with primers Daudi uni1-AGGCCTATGAC-CCCCACC (SEQ ID NO:8) and Daudi rev2-CATTCCTC-CCAGACCCCA (SEQ ID NO:9). All primers disclosed herein are listed in 5' to 3' orientation.

In a specific embodiment disclosed herein, the invention relates to the nucleic acid sequence of the human TCL-1 gene. In a preferred, but not limiting, aspect of the invention, a human TCL-1 cDNA sequence is that present in plasmid PA11.5 as deposited with the ATCC and assigned ATCC Accession Number 75923. Such a sequence can be cloned and sequenced, for example, as described in Section 6, infra. The invention also relates to nucleic acid sequences hybridizable or complementary to the foregoing sequences or equivalent to the foregoing sequences in that the equivalent nucleic acid sequences also encode a TCL-1 protein product.

Nucleic acids encoding fragments and derivatives of TCL-1 are additionally described infra.

In a preferred aspect, polymerase chain reaction (PCR) is used to amplify the desired nucleic acid sequence in the library by using oligonucleotide primers representing known TCL-1 sequences. Such primers are disclosed infra in Section 7 and may be used to amplify sequences of interest from an RNA or DNA source, preferably a cDNA library. PCR can be carried out, e.g., by use of a Perkin-Elmer Cetus thermal cycler and Taq polymerase (Gene Amp). The DNA being amplified can include mRNA or cDNA or genomic DNA from any eukaryotic species. One can choose to synthesize several different degenerate primers, for use in the PCR reactions. It is also possible to vary the stringency of hybridization conditions used in priming the PCR reactions, to allow for greater or lesser degrees of nucleotide sequence homology between the TCL-1 gene being cloned and the known TCL-1 gene. Other means for primer dependent amplification of nucleic acids are known to those of skill in the art and can be used.

After successful amplification of a segment of a TCL-1 gene (e.g., an allelic or polymorphic variant or species homolog of a known TCL-1 gene) that segment may be molecularly cloned and sequenced, and utilized as a probe to isolate a complete cDNA or genomic clone. This, in turn, will permit the determination of the gene's complete nucleotide sequence, the analysis of its expression, and the production of its protein product for functional analysis, as described infra. In this fashion, additional genes encoding TCL-1 proteins may be identified. Alternatively, the TCL-1 gene of the present invention may be isolated through an exon trapping system, as is disclosed infra, in Section 6, using genomic DNA (Nehls et al., 1994, *Oncogene* 9(8):2169-2175; Verna et al., 1993, *Nucleic Acids Res.* 21(22):5198:5202; and Auch et al., 1990, *Nucleic Acids Res.* 18(22):6743-6744).

Potentially, any eukaryotic cell can serve as the nucleic acid source for the molecular cloning of the TCL-1 gene. The nucleic acid sequences encoding TCL-1 can be isolated from, for example, human, porcine, bovine, feline, avian, equine, canine, rodent, as well as additional primate sources. The DNA may be obtained by standard procedures known in the art from, for example, cloned DNA (e.g., a DNA "library"), by chemical synthesis, by cDNA cloning, or by the cloning of genomic DNA, or fragments thereof, purified from a desired cell. (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) A preferred source is cDNA of leukemic cells in which the leukemia is associated with a 14q32.1 chromosomal abnormality. Clones derived from genomic DNA may contain regulatory and intron DNA regions in addition to coding regions while clones derived from cDNA will contain only TCL-1 exon sequences. In a particular embodiment of the present invention, a genomic sequence is one that is not more than 10 kilobases (kb), or not more than 20 kb, or not more than 50 kb or not more than 70 kb. Whatever the source, the gene should be molecularly cloned into a suitable vector for propagation of the gene. In a particular embodiment, a preferred source of nucleic acid for the isolation of TCL-1 gene sequences is from pre B-cells.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, a TCL-1 gene of the present invention or its specific RNA, or a fragment thereof, such as a probe or primer, may be isolated and labeled and then used in hybridization assays to detect a generated TCL-1 gene (Benton, W. and Davis, R., 1977, *Science* 196:180; Grunstein, M. And Hogness, D., 1975, *Proc. Natl. Acad. Sci. USA* 72:3961). Those DNA fragments sharing substantial sequence homology to the probe will hybridize under stringent conditions. The phrase "stringent conditions" as used herein refers to those hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium pyrophosphate, 5× Denhardt's solution, sonicated salmon sperm DNA (50 g/ml), 0.1% SDS, and 10% dextran sulfate at 42° C., with washes at 42° C. in 0.2×SSC and 0.1% SDS.

It is also possible to identify the appropriate fragment by restriction enzyme digestion(s) and comparison of fragment sizes with those expected according to a known restriction map. Further selection can be carried out on the basis of the properties of the gene. Alternatively, the presence of the gene may be detected by assays based on the physical, chemical, or immunological properties of its expressed product. For example, cDNA clones, or genomic DNA clones which hybrid-select the proper mRNAs, can be selected which produce a protein that has similar or identical electrophoretic migration, isoelectric focusing behavior, proteolytic digestion maps, binding activity or antigenic properties as known for TCL-1. Alternatively, the TCL-1 protein may be identified by binding of labeled antibody to the putatively TCL-1 expressing clones, e.g., in an ELISA (enzyme-linked immunosorbent assay)-type procedure.

The TCL-1 gene can also be identified by mRNA selection by nucleic acid hybridization followed by in vitro translation. In this procedure, fragments are used to isolate complementary mRNAs by hybridization. Such DNA fragments may represent available, purified TCL-1 DNA of another TCL-1 gene. Immunoprecipitation analysis or functional assays of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against TCL-1 protein. A radiolabelled TCL-1 cDNA can be synthesized using the selected mRNA (from the adsorbed polysomes) as a template. The radiolabelled mRNA or cDNA may then be used as a probe to identify the TCL-1 DNA fragments from among other genomic DNA fragments.

Alternatives to isolating the TCL-1 genomic DNA include, but are not limited to, chemically synthesizing the gene sequence itself from a known sequence or making cDNA to the mRNA which encodes the TCL-1 protein. For example, RNA useful in cDNA cloning of the TCL-1 gene can be isolated from cells which express TCL-1, e.g., pre-B acute lymphoblastic leukemia cells or endemic Burkitt's lymphoma cells which express cell surface IgM and do not secrete immunoglobulin. Other methods are known to those of skill in the art and are within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and TCL-1 gene may be modified by homopolymeric tailing. Recombinant molecules can be introduced into host cells via transformation, transfection, infection, electroporation, or other methods known to those of skill in the art, so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning vector.

In specific embodiments, transformation of host cells with recombinant DNA molecules that incorporate the isolated TCL-1 gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

Oligonucleotides containing a portion of the TCL-1 coding or non-coding sequences, or which encode a portion of the TCL-1 protein (e.g., primers for use in PCR) can be synthesized by standard methods commonly known in the art. Such oligonucleotides preferably have a size in the range of 8 to 25 nucleotides. In a particular embodiment herein, such oligonucleotides have a size in the range of 15 to 25 nucleotides or 18 to 25 nucleotides.

5.2. Expression of the TCL-1 Gone

In accordance with the present invention, polynucleotide sequences coding for a TCL-1 protein, derivative, e.g. fragment, or analog thereof, can be inserted into an appropriate expression vector, i.e., a vector which contains the necessary elements for the transcription and translation of the inserted protein-coding sequence, for the generation of recombinant DNA molecules that direct the expression of a TCL-1 protein. Such TCL-1 polynucleotide sequences, as well as other polynucleotides or their complements, may also be used in nucleic acid hybridization assays, Southern and Northern blot analysis, etc. In a specific embodiment, a human TCL-1 gene, or a sequence encoding a functionally active portion of a human TCL-1 gene is expressed. In yet another embodiment, a derivative or fragment of a human TCL-1 gene is expressed.

Due to the inherent degeneracy of the genetic code, other DNA sequences which encode substantially the same or a functionally equivalent TCL-1 amino acid sequence, is within the scope of the invention. Such DNA sequences include those which are capable of hybridizing to the human TCL-1 sequence under stringent conditions.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within an TCL-1 sequence, which result in a silent change thus producing a functionally equivalent TCL-1 protein. Such amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine.

The DNA sequences of the invention may be engineered in order to alter a TCL-1 coding sequence for a variety of ends including but not limited to alterations which modify processing and expression of the gene product. For example, mutations may be introduced using techniques which are well known in the art, e.g., site-directed mutagenesis, to insert new restriction sites, to alter phosphorylation, etc.

In another embodiment of the invention, a TCL-1 gene sequence or a derivative thereof is ligated to a non-TCL-1 sequence to encode a chimeric fusion protein. A fusion protein may also be engineered to contain a cleavage site located between a TCL-1 sequence and the non-TCL-1 protein sequence, so that the TCL-1 protein may be cleaved away from the non-TCL-1 moiety. In a specific embodiment, the TCL-1 amino acid sequence present in the fusion protein consists of at least 10 contiguous amino acids, at least 25 contiguous amino acids, at least 50 contiguous amino acids, at least 75 contiguous amino acids, at least 100 contiguous amino acids, or at least 114 amino acids of the TCL-1 protein sequence.

In an alternate embodiment of the invention, the coding sequence of a TCL-1 is synthesized in whole or in part, using chemical methods well known in the art. See, for example, Caruthers et al., 1980, *Nuc. Acids Res. Symp. Ser.* 7:215-233; Crea and Horn, 1980, *Nuc. Acids Res.* 9(10):2331; Matteucci and Caruthers, 1980,*Tetrahedron Letters* 21:719; and Chow and Kempe, 1981, *Nuc. Acids Res.* 9(12):2807-2817. Alternatively, the protein itself could be produced using chemical methods to synthesize an TCL-1 amino acid sequence in whole or in part. For example, peptides can be synthesized by solid phase techniques, cleaved from the resin, and purified by preparative high performance liquid chromatography. (e.g., see Creighton, 1983, *Proteins Structures And Molecular Principles*, W.H. Freeman and Co., N.Y. pp. 50-60). The composition of the synthetic peptides may be confirmed by amino acid analysis or sequencing (e.g., the Edman degradation procedure; see Creighton, 1983, *Proteins, Structures and Molecular Principles*, W.H. Freeman and Co., N.Y., pp. 34-49.

In order to express a biologically active TCL-1 protein or derivative thereof, a polynucleotide sequence encoding a TCL-1 protein, or a derivative thereof, is inserted into an appropriate expression vector, i.e., a vector which contains the necessary elements for the transcription and translation of the inserted coding sequence. The TCL-1 gene products as well as host cells or cell lines transfected or transformed with recombinant TCL-1 expression vectors can be used for a variety of purposes. These include but are not limited to generating antibodies (i.e., monoclonal or polyclonal) that immunospecifically bind a TCL-1 protein. Anti-TCL-1 antibodies can be used in detecting or measuring levels of a TCL-1 protein in patient samples.

5.3. Expression Systems

Methods which are well known to those skilled in the art can be used to construct expression vectors containing a TCL-1 coding sequence and appropriate transcriptional/ translational control signals. These methods include in vitro recombinant DNA techniques, synthetic techniques and in vivo recombination/genetic recombination. See, for example, the techniques described in Sambrook et al., 1989, *Molecular Cloning, A Laboratory Manual* 2d ed., Cold Spring Harbor Laboratory, N.Y. and Ausubel et al., 1989, *Current Protocols in Molecular Biology*, Greene Publishing Associates and Wiley Interscience, N.Y.

A variety of host-expression vector systems may be utilized to express a TCL-1 coding sequence. These include but are not limited to microorganisms such as bacteria transformed with recombinant bacteriophage DNA, plasmid DNA or cosmid DNA expression vectors containing an TCL-1 coding sequence; yeast transformed with recombinant yeast expression vectors containing an TCL-1 coding sequence; insect cell systems infected with recombinant virus expression vectors (e.g., baculovirus) containing an TCL-1 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing an TCL-1 coding sequence; or animal cell systems. The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of an TCL-1 DNA, SV40-, BPV- and EBV-based vectors may be used with an appropriate selectable marker.

In bacterial systems, a number of expression vectors may be advantageously selected depending upon the use intended for the TCL-1 protein expressed. For example, when large quantities of TCL-1 protein are to be produced for the generation of antibodies, vectors which direct the expression of high levels of fusion protein products that are readily purified may be desirable. Such vectors include but are not limited to the *E. coli* expression vector pUR278 (Ruther et al., 1983, *EMBO J.* 2:1791), in which the TCL-1 coding sequence may be ligated into the vector in frame with the lac Z coding region so that a hybrid AS-lac Z protein is produced; pIN vectors (Inouye & Inouye, 1985, *Nucleic acids Res.* 13:3101-3109; Van Heeke & Schuster, 1989, *J. Biol. Chem.* 264:5503-5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

In yeast, a number of vectors containing constitutive or inducible promoters may be used. For a review see, *Current Protocols in Molecular Biology*, Vol. 2, 1988, Ed. Ausubel et al., Greene Publish. Assoc. & Wiley Interscience, Ch. 13; Grant et al., 1987, *Expression and Secretion Vectors for Yeast*, in Methods in Enzymology, Ed. Wu & Grossman, 1987, Acad. Press, N.Y. 153:516-544;. Glover, 1986, *DNA Cloning Vol. II*, IRL Press, Wash., D.C., Ch. 3; and Bitter, 1987, Heterologous Gene Expression in Yeast, *Methods in Enzymology*, Eds. Berger & Kimmel, Acad. Press, N.Y. 152:673-684; and *The Molecular Biology of the Yeast Saccharomyces*, 1982, Eds. Strathern et al., Cold Spring Harbor Press, Vols. I and II.

In cases where plant expression vectors are used, the expression of an TCL-1 coding sequence may be driven by any of a number of promoters. For example, viral promoters such as the 35S RNA and 19S RNA promoters of CaMV (Brisson et al., 1984, *Nature* 310:511-514), or the coat protein promoter of TMV (Takamatsu et al., 1987, *EMBO J.* 6:307-311) may be used; alternatively, plant promoters such as the small subunit of RUBISCO (Coruzzi et al., 1984, *EMBO J.* 3:1671-1680; Broglie et al., 1984, *Science* 224:838-843); or heat shock promoters, e.g., soybean hsp17.5-E or hsp17.3-B (Gurley et al., 1986, *Mol. Cell. Biol.* 6:559-565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, *Methods for Plant Molecular Biology*, Academic Press, NY, Section VIII, pp. 421-463; and Grierson & Corey, 1988, *Plant Molecular Biology*, 2d Ed., Blackie, London, Ch. 7-9.

An alternative expression system which could be used to express a TCL-1 gene is an insect system. In one such system, *Autographa californica* nuclear polyhedrosis virus (AcNPV) is used as a vector to express foreign genes. The virus grows in *Spodoptera frugiperda* cells. A TCL-1 coding sequence may be cloned into non-essential regions (for example the polyhedrin gene) of the virus and placed under control of an AcNPV promoter (for example, the polyhedrin promoter). Successful insertion of a TCL-1 coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, *J. Virol.* 46:584; Smith, U.S. Pat. No. 4,215,051).

In mammalian host cells, a number of viral based expression systems may be utilized. In cases where an adenovirus is used as an expression vector, a TCL-1 coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a TCL-1 in infected hosts. (e.g., see Logan & Shenk, 1984, *Proc. Natl. Acad. Sci. USA* 81:3655-3659). Alternatively, the vaccinia 7.5 K promoter may be used. (See, e.g., Mackett et al., 1982, *Proc. Natl. Acad. Sci. USA* 79:7415-7419; Mackett et al., 1984, *J. Virol.* 49:857-864; Panicali et al., 1982, *Proc. Natl. Acad. Sci. USA* 79:4927-4931).

Specific initiation signals may also be required for efficient translation of an inserted TCL-1 coding sequences. These signals include the ATG initiation codon and adjacent sequences. In cases where an entire TCL-1 gene, including its own initiation codon and adjacent sequences, is inserted into the appropriate expression vector, no additional translational control signals may be needed. However, in cases where only a portion of a TCL-1 coding sequence is inserted, lacking the 5' end, exogenous translational control signals, including the ATG initiation codon, must be provided. Furthermore, the initiation codon must be in phase with the reading frame of a TCL-1 coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, *Methods in Enzymol.* 153:516-544).

In addition, a host cell strain may be chosen which modulates the expression of the inserted sequences, or modifies and processes the gene product in the specific fashion desired. Such modifications (e.g., phosphorylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, and phosphorylation of the gene product may be used. Such mammalian host cells include but are not limited to CHO, VERO, BHK, HeLa, COS, MDCK, 293, WI38, etc.

For long-term, high-yield production of recombinant proteins, stable expression is preferred. For example, cell lines which stably express a TCL-1 protein may be engineered. Rather than using expression vectors which contain viral origins of replication, host cells can be transformed with TCL-1 DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express a TCL-1 protein. The present invention provides a method for producing a recombinant TCL-1 protein comprising culturing a host cell transformed with a recombinant expression vector encoding a TCL-1 protein such that the TCL-1 protein is expressed by the cell and recovering the expressed TCL-1 protein.

A number of selection systems may be used, including but not limited to the herpes simplex virus thymidine kinase (Wigler et al., 1977, *Cell* 11:223), hypoxanthine-guanine phosphoribosyltransferase (Szybalska & Szybalski, 1962, *Proc. Natl. Acad. Sci. USA* 48:2026), and adenine phosphoribosyltransferase (Lowy et al., 1980, *Cell* 22:817) genes can be employed in tk-, hgprt- or aprt-cells, respectively. Also, antimetabolite resistance can be used as the basis of selection for dhfr, which confers resistance to methotrexate (Wigler et al., 1980, *Natl. Acad. Sci. USA* 77:3567; O'Hare et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (Colberre-Garapin et al., 1981, *J. Mol. Biol.* 150:1); and hygro, which confers resistance to hygromycin (Santerre et al., 1984, *Gene* 30:147). Recently, additional selectable genes have been described, namely trpB, which allows cells to utilize indole in place of tryptophan; hisD, which allows cells to utilize histinol in place of histidine (Hartman & Mulligan, 1988, *Proc. Natl. Acad. Sci. USA* 85:8047); and ODC (ornithine decarboxylase) which confers resistance to the ornithine decarboxylase inhibitor, 2-(difluoromethyl)-DL-ornithine, DFMO (McConlogue, L., 1987, In: *Current Communications in Molecular Biology*, Cold Spring Harbor Laboratory, Ed.).

5.4. Identification of Transfectants or Transformants that Express TCL-1

The host cells which contain the coding sequence and which express the biologically active gene product may be identified by at least four general approaches; (a) DNA-DNA or DNA-RNA hybridization; (b) the presence or absence of "marker" gene functions; (c) assessing the level of transcription as measured by the expression of TCL-1 mRNA transcripts in the host cell; and (d) detection of the gene product as measured by immunoassay or by its biological activity.

In the first approach, the presence of the TCL-1 coding sequence inserted in the expression vector can be detected by DNA-DNA or DNA-RNA hybridization using probes comprising nucleotide sequences that are homologous to the TCL-1 coding sequence, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the human TCL-1 coding sequence is inserted within a marker gene sequence of the vector, recombinant cells containing the TCL-1 coding sequence can be identified by the absence of the marker gene function. Alternatively, a marker gene can be placed in tandem with a TCL-1 sequence under the control of the same or different promoter used to control the expression of the TCL-1 coding sequence. Expression of the marker in response to induction or selection indicates expression of the TCL-1 coding sequence.

In the third approach, transcriptional activity of a TCL-1 gene can be assessed by hybridization assays. For example, RNA can be isolated and analyzed by Northern blot using a probe having sequence homology to a TCL-1 coding sequence or transcribed noncoding sequence or particular portions thereof. Alternatively, total nucleic acid of the host cell may be extracted and quantitatively assayed for hybridization to such probes.

In the fourth approach, the levels of a TCL-1 protein product can be assessed immunologically, for example by Western blots, immunoassays such as radioimmuno-precipitation, enzyme-linked immunoassays and the like.

5.5. Purification of the Expressed Gene Product

Once a recombinant which expresses the TCL-1 gene sequence is identified, the gene product can be analyzed. This is achieved by assays based on the physical or functional properties of the product, including radioactive labelling of the product followed by analysis by gel electrophoresis, immunoassay, or other detection methods known to those of skill in the art.

Once the TCL-1 protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay.

Alternatively, once a TCL-1 protein produced by a recombinant is identified, the amino acid sequence of the protein can be deduced from the nucleotide sequence of the chimeric gene contained in the recombinant. As a result, the protein can be synthesized by standard chemical methods known in the art. (e.g., see Hunkapiller et al., 1984, *Nature* 310:105-111).

In a specific embodiment of the present invention, such TCL-1 proteins, whether produced by recombinant DNA techniques or by chemical synthetic methods, include but are not limited to those containing, as a primary amino acid sequence, all or part of the amino acid sequence substantially as depicted in FIG. 3A (SEQ ID NO:2), as well as fragments and other derivatives, and analogs thereof.

5.6. Generation of Antibodies to TCL-1

According to the invention, TCL-1 protein, its fragments or other derivatives, or analogs thereof, may be used as an immunogen to generate antibodies which recognize such an immunogen. Such antibodies include but are not limited to polyclonal, monoclonal, chimeric, single chain, Fab fragments, and an Fab expression library. In a specific embodiment, antibodies to a human TCL-1 protein are produced.

Various procedures known in the art may be used for the production of polyclonal antibodies to a TCL-1 protein or derivative or analog. For the production of antibody, various host animals can be immunized by injection with the native TCL-1 protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *corynebacterium parvum*.

In a specific example, the 14 kDa protein of the TCL-1 gene expressed in bacteria was used to immunize rabbits against TCL-1. Such antibodies recognized the 14 kDa TCL-1 protein in a variety of leukemia and lymphoma cells by Western Blot and by immunoprecipitation.

For preparation of monoclonal antibodies directed toward a TCL-1 protein sequence or analog thereof, any technique which provides for the production of antibody molecules by continuous cell lines in culture may be used. For example, the hybridoma technique originally developed by Kohler and Milstein (1975, *Nature* 256:495-497), as well as the trioma technique, the human B-cell hybridoma technique (Kozbor et al., 1983, *Immunology Today* 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, *Proc. Natl. Acad. Sci. USA* 80:2026-2030) or by transforming human B cells with EBV virus in vitro (Cole et al., 1985, in *Monoclonal Antibodies and Cancer Therapy*, Alan R. Liss, pp. 77-96). In fact, according to the invention, techniques developed for the production of "chimeric antibodies" (Morrison et al., 1984, *Proc. Natl. Acad. Sci. USA* 81:6851-6855; Neuberger et al., 1984, *Nature* 312:604-608; Takeda et al., 1985, *Nature* 314:452-454) by splicing the genes from a mouse antibody molecule specific for TCL-1 together with genes from a human antibody molecule of appropriate biological activity can be used; such antibodies are within the scope of this invention.

According to the invention, techniques described for the production of single chain antibodies (U.S. Pat. No. 4,946,778) can be adapted to produce TCL-1-specific single chain antibodies. An additional embodiment of the invention utilizes the techniques described for the construction of Fab expression libraries (Huse et al., 1989, *Science* 246:1275-

1281) to allow rapid and easy identification of monoclonal Fab fragments with the desired specificity for TCL-1 proteins, derivatives, or analogs.

Antibody fragments which contain the idiotype of the molecule can be generated by known techniques. For example, such fragments include but are not limited to: the F(ab')$_2$ fragment which can be produced by pepsin digestion of the antibody molecule; the. Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g. ELISA (enzyme-linked immunosorbent assay). For example, to select antibodies which recognize a specific domain of a TCL-1 protein, one may assay generated hybridomas for a product which binds to a TCL-1 fragment containing such domain. For selection of an antibody specific to human TCL-1, one can select on the basis of positive binding to human TCL-1 and a lack of binding to, for example, mouse TCL-1.

The foregoing antibodies can be used in methods known in the art relating to the localization and activity of the protein sequences of the invention (e.g., see Section 5.7, infra), e.g., for imaging these proteins, measuring levels thereof in appropriate physiological samples, etc.

5.7. Structure of the TCL-1 Gene and Protein

The structure of the TCL-1 gene and protein can be analyzed by various methods known in the art.

5.7.1. Genetic Analysis

The cloned DNA or cDNA corresponding to the TCL-1 gene can be analyzed by methods including but not limited to Southern hybridization (Southern, E. M., 1975, *J. Mol. Biol.* 98:503-517), Northern hybridization (see, e.g., Freeman et al., 1983, *Proc. Natl. Acad. Sci. USA* 80:4094-4098), restriction endonuclease mapping (Maniatis, T., 1982, Molecular Cloning, A Laboratory, Cold Spring Harbor, N.Y.), and DNA sequence analysis. Polymerase chain reaction (PCR; U.S. Pat. Nos. 4,.683,202, 4,683,195, and 4,889,818; *Proc. Natl. Acad. Sci. USA* 85:7652-7656; Ochman et al., 1988, *Genetics* 120:621-623; Loh et al., 1989, *Science* 243:217-220) followed by Southern hybridization with a TCL-1-specific probe can allow the detection of the TCL-1 gene in DNA from various cell types. In one embodiment, Southern hybridization may be used to determine the genetic linkage of TCL-1. PCR followed by hybridization assay can also be used to detect or measure TCL-1 RNA or 14q32.1 chromosomal abnormalities. Northern hybridization analysis can be used to determine the expression levels of the TCL-1 gene. Other assays are described in Section 5.8.1. Various cell types, at various states of development or activity can be tested for TCL-1 expression. The stringency of the hybridization conditions for both Southern and Northern hybridization, or dot blots, can be manipulated to ensure detection of nucleic acids with the desired degree of relatedness to the specific TCL-1 probe used.

Restriction endonuclease mapping can be used to roughly determine the genetic structure of the TCL-1 gene. Restriction maps derived by restriction endonuclease cleavage can be confirmed by DNA sequence analysis.

DNA sequence analysis can be performed by any techniques known in the art, including but not limited to the method of Maxam and Gilbert (1980, *Meth. Enzymol.* 65:499-560), the Sanger dideoxy method (Sanger et al., 1977, *Proc. Natl. Acad. Sci. USA* 74:5463), the use of T7 DNA polymerase (Tabor and Richardson, U.S. Pat. No. 4,795,699), or use of an automated DNA sequenator (e.g., Applied Biosystems, Foster City, Calif.). The cDNA sequence of a representative TCL-1 gene comprises the sequence substantially as depicted in FIG. 3A (SEQ ID NO: 1), and described in Section 6, infra.

5.7.2. Protein Analysis

The amino acid sequence of the TCL-1 protein can be derived by deduction from the DNA sequence, or alternatively, by direct sequencing of the protein, e.g., with an automated amino acid sequencer. The amino acid sequence of a representative TCL-1 protein comprises the sequence substantially as depicted in FIG. 3A (SEQ ID NO: 2), and detailed in Section 6, infra, with the representative mature protein that is shown by amino acid numbers 1-114.

The TCL-1 protein sequence can be further characterized by a hydrophilicity analysis (Hopp, T. and Woods, K., 1981, *Proc. Natl. Acad. Sci. USA* 78:3824). A hydrophilicity profile can be used to identify the hydrophobic and hydrophilic regions of the TCL-1 protein and the corresponding regions of the gene sequence which encode such regions.

Secondary structural analysis (Chou, P. and Fasman, G., 1974, *Biochemistry* 13:222) can also be done, to identify regions of the TCL-1 protein that assume specific secondary structures.

Manipulation, translation, and secondary structure prediction, as well as open reading frame prediction and plotting, can also be accomplished using computer software programs available in the art.

Other methods of structural analysis can also be employed. These include but are not limited to X-ray crystallography (Engstom, A., 1974, *Biochem. Exp. Biol.* 11:7-13) and computer modeling (Fletterick, R. and Zoller, M. (eds.), 1986, Computer Graphics and Molecular Modeling, in Current Communications in Molecular Biology, Cold Spring Harbor Laboratory, Cold Spring Harbor, N.Y.).

5.8. Uses of TCL-1 and its TCL-1 Protein Product and Antibodies Thereto

Chromosomal translocations and inversions associated with the TCL-1 locus on chromosome 14, e.g., t(14.:14)(q11; q32) chromosome translocation, inv(14)(q11;q32) chromosome inversion, and t(7:14)(q35;q32) chromosome translocation, are associated with several post-thymic types of T-cell leukemias, including, but not limited to, T-prolymphocytic leukemias (T-PLL) (Brito-Babapulle and Catovsky, 1991, *Cancer Genet. Cytogenet.* 55:1-9), acute and chronic leukemias associated with the immunodeficiency syndrome ataxia-telangiectasia (AT) (Russo et al., 1988, *Cell* 53:137-144; Russo et al., 1989, *Proc. Natl. Acad. Sci. USA* 86:602-606), and adult T-cell leukemia (Virgilio et al., 1993, *PNAS* 90:9275-9279). In some cases of AT-associated translocations, in T-cell leukemia and lymphoma involving the 14q32.1 band, clonal expansion of cells carrying abnormalities in 14q32.1 have been documented in some cases prior to the development of overt malignancy (Russo, et al. (1988) *Cell* vol. 53, pg. 137-144). Therefore, a TCL-1 polynucleotide, its TCL-1 protein product and antibodies thereto can be used for diagnostic and/or therapeutic/prophylactic purposes for the above described diseases, as well as other disorders associated with chromosomal translocations and inversions associated with the TCL-1 locus and/or, increased expression of TCL-1 RNA or protein. A TCL-1 polynucleotide, its TCL-1 protein product and antibodies thereto may be used for therapeutic/prophylactic purposes alone or in combination with other therapeutics useful in the treatment of T-cell leukemias. Such molecules can also be used in diagnostic assays, such as immunoassays, to detect, prognose, diagnose, or monitor various conditions, diseases, and disorders associated with TCL-1 gene expression or monitor the treatment thereof. Accordingly, in specific embodiments, T-cell malignancies or premalignant changes in such tissues is diagnosed by detecting increased TCL-1 expression in patient samples relative to the level of TCL-1 expression in an analogous non-malignant sample (from the patient or another person, as determined experimentally or as is known as a standard level in such samples). For diagnostic purposes, a TCL-1 polynucleotide may be used to detect TCL-1 gene expression or increased TCL-1 gene expression in disease states, such as, T-cell leukemias and lymphomas. For therapeutic purposes, a TCL-1 protein can be used to make anti-TCL-1 antibodies that may neutralize the activity of TCL-1. Included within the scope of the present invention are oligonucleotide sequences, that include antisense RNA and DNA molecules and ribozymes, that function to inhibit expression of a TCL-1 RNA or protein.

5.8.1. Diagnostic Uses

As illustrated infra, the TCL-1 gene sequence is associated with disease states associated with chromosome 14 translocations and inversions around the TCL-1 locus, is preferentially expressed early in T and B lymphocyte differentiation and demonstrates a high level of expression in cells from patients diagnosed with T-PLL carrying an inversion of chromosome 14, inv(14)(q11;q32) or patients carrying a t(14:14) (q11;q32) chromosome translocation. Accordingly, TCL-1 gene sequences may be used diagnostically for the detection of diseases states resulting from chromosomal abnormalities, e.g., translocations, inversions and deletions, involving the TCL-1 locus of chromosome 14. Nucleic acids comprising TCL-1 nucleotide sequences of at least 8 nucleotides, at least 15 nucleotides, at least 25 nucleotides, at least 50 nucleotides, at least 100 nucleotides, at least 200 nucleotides, at least 300 nucleotides, or at least 387 nucleotides up to 1324 nucleotides of SEQ ID NO: 1 may be used as probes in hybridization assays for the detection and measurement of TCL-1 gene. Nucleic acids of not more than 5 kilobases, of not more than 10 kilobases, not more than 25 kilobases, not more than 50 kilobases or not more than 70 kilobases which are hybridizable to a TCL-1 gene, cDNA, or complementary strand can be used as probes in hybridization assays for the detection and measurement of TCL-1 nucleotide sequences. As an example, the TCL-1 DNA sequence may be used in hybridization assays, e.g., Southern or Northern analysis, including in situ hybridization assays, of patient's samples to diagnose abnormalities of TCL-1 expression. Hybridization assays can be used to detect, prognose, diagnose, or monitor conditions, disorders, or disease states, such as T-cell malignancies, associated with aberrant changes in TCL-1 expression and/or activity as described supra. In particular, such a hybridization assay is carried out by a method comprising contacting a sample containing nucleic acid with a nucleic acid probe capable of hybridizing to TCL-1 DNA or RNA, under conditions such that hybridization can occur, and detecting or measuring any resulting hybridization. In particular, hybridization assays can be used to detect the presence of abnormalities associated with increased expression of TCL-1 mRNA, by hybridizing mRNA or cDNA from a patient sample to a TCL-1 probe, and measuring the amount of resulting hybridization. For example, assays which can be used include, but are not limited to Northern blots, Dot blots, reverse transcriptase PCR, etc. A preferred hybridization assay is Northern blot analysis of a patient sample using TCL-1 gene probes of at least 15 polynucleotides up to the full length cDNA sequence shown in FIG. 3A. Another preferred hybridization assay is in situ hybridization analysis of a patient sample using anti-TCL-1 antibodies or TCL-1 nucleotide hybridization probes. Such techniques are well known in the art, and are in fact the basis of many commercially available diagnostic kits.

As used herein, patient samples which can be used include, but are not limited to, fresh or frozen tissue samples, which can be used in in situ hybridization assays; cell or tissue samples containing T-lymphocytes and, in general, patient samples containing nucleic acid, such as peripheral blood lymphocytes (PBL) and T-lymphocytes which can be used in assays that measure or quantitate TCL-1 nucleic acid.

Polynucleotide sequences of TCL-1 consisting of at least 8 to 25 nucleotides that are useful as primers in primer dependent nucleic acid amplification methods may be used for the detection of TCL-1 gene sequences in patient samples. Primer dependent nucleic acid amplification methods useful in the present invention include, but are not limited to, polymerase chain reaction (PCR), competitive PCR, cyclic probe reaction, and ligase chain reaction. Such techniques are well known by those of skill in the art. A preferred nucleic acid amplification method of the present invention is reverse transcriptase PCR (RT-PCR) Siebert et al., 1992, *Nature* 359:557-558).

In a particular embodiment of the present invention, each primer of a pair of primers for use in a primer dependent nucleic acid amplification method is selected from a different exon of the genomic TCL-1 nucleotide sequences. For example, if one primer of a pair or primers is selected from exon 1 of the TCL-1 genomic sequence, the second primer will be selected from exon 2, 3 or 4 of the TCL-1 genomic sequence. As another example, if one primer of a pair of primers is selected from exon 2 of the TCL-1 genomic sequence, the second primer will be selected from exon 1, 3, or 4 of the TCL-1 genomic sequence. By selecting each primer of a pair of primers for use in a primer dependent nucleic acid amplification method from a different exon, amplified genomic nucleotide sequences can be distinguished from amplified cDNA nucleotide sequences due to the size difference of the resulting amplified sequences. Resulting amplified genomic nucleotide sequences will contain amplified intron sequences and will be of a larger size than amplified cDNA nucleotide sequences that will not contain amplified intron sequences. For amplification of cDNA nucleotide sequences, the primer sequences should be selected from exons sequences that are sufficiently far enough apart to provide a detectable amplified nucleotide sequence.

The TCL-1 gene sequences of the present invention may be used diagnostically for the detection of chromosome 14 abnormalities, in particular translocations t(14:14) (q11:q32) and inv(14) (q11;q32) inversion at 14q32.1. Accordingly, the present invention provides a process for detecting a target sequence indicative of or including a chromosome 14 abnormality in a sample, comprising the steps of amplifying the target sequence in the sample using a first primer of 8 to 25 nucleotides, preferably 18-25 nucleotides, complementary to the nucleotide sequence of SEQ ID NO: 1 or SEQ ID NO: 3, and a second primer complementary to a region teleomeric or centromeric to the TCL-1 gene and detecting any resulting amplified target sequence in which the presence of the amplified target sequence is indicative of the abnormality. The present invention also provides a method of diagnosing a T-cell malignancy associated with chromosome 14 abnormalities in a patient comprising, detecting said chromosome 14 abnormality according to the method above in which the presence of the amplified target sequence indicates the presence of a T-cell malignancy in the patient. The resultant amplified target sequence can be detected on gel electrophoresis and compared with a normal sample-or standard that does not contain a chromosome 14 abnormality. Virgilio et al., supra, disclose polynucleotide sequences useful as second primers. Other polynucleotide sequences useful as second primers can be selected from the T-cell receptor α/δ locus, the T-cell receptor β chain, or if the chromosome 14 abnormality involves an inversion, a polynucleotide sequence 5' to exon 1 of the TCL-1 gene, or if the chromosome abnormality involves a translocation, a polynucleotide sequence 3' to the 3' intron of the TCL-1 gene. The amplification of genomic DNA target sequences may require generating long PCR products. PCR techniques for generating long PCR products are described in *Science* (1994) 263:1564-1565; PCR kits for generating long PCR products are available from Perkin Elmer and Takara Shuzo Co., Ltd. The present invention also provides a method for detecting a target nucleotide sequence indicative of or including at least a portion of a chromosome 14 abnormality in a nucleic acid sample, comprising the steps of hybridizing the sample with a nucleic acid probe of not more than 10 kilobases, comprising in the range of 15-1324 nucleotides complementary to at least a portion of the nucleotide sequence of SEQ ID NO: 1; and detecting or measuring the amount of any resulting hybridization between the probe and the target sequence within the sample. The resultant hybridization between the probe and the target sequence within the sample can be detected using gel electrophoresis and can be compared to a target sequence from a normal sample or standard that does not contain a chromosome 14 abnormality. The present invention also provides a method of diagnosing a T-cell malignancy associated with chromosome 14 abnormalities in a patient comprising, detecting said chromosome 14 abnormality according to the method above in which the presence of the amplified target sequence indicates the presence of a T-cell malignancy in the patient. Absolute complementarity between a hybridization probe and a target sequence, although preferred, is not required. A sequence "complementary to at least a portion of", as referred to herein, means a sequence having sufficient complementarity to be able to hybridize with the nucleic acid, forming a stable hybridization complex. The ability to hybridize will depend on both the degree of complementarity and the length of the nucleic acid. Generally, the longer the hybridizing nucleic acid, the more base mismatches with a TCL-1 RNA it may contain and still form a stable duplex (or triplex, as the case may be). One skilled in the art can ascertain a tolerable degree of mismatch by use of standard procedures to determine the melting point of the hybridized complex.

An additional aspect of the present invention relates to diagnostic kits for the detection or measurement of TCL-1 gene sequences and TCL-1 protein. Accordingly, the present invention provides a diagnostic kit comprising, in a container a compound comprising a probe of not more than 10 kilobases and comprising in the range of 15-1324 nucleotides of the nucleotide sequence of SEQ ID NO: 1 or its complement. Alternatively, the present invention provides a diagnostic kit comprising, in one or more containers, a pair of primers of at least 8-25 nucleotides in which at least one of said primers is hybridizable to SEQ ID NO: 1 or its complement and wherein said primers are capable of priming cDNA synthesis in an amplification reaction. The present invention also provides a diagnostic kit in which at least one of the primers is hybridizable to SEQ ID NO: 1 or its complement and in which one of the primers is hybridizable to a DNA sequence located telomeric or centromeric to the TCL-1 gene. In a specific embodiment, one of the foregoing compounds of the container can be detectably labeled.

The amplification reaction of the present invention may be a polymerase chain reaction, competitive PCR and competitive reverse-transcriptase PCR (Clementi et al., 1994, *Genet Anal Tech Appl* 11(1):1-6 and Siebert et al., 1992, *Nature* 359:557-558); cyclic probe reaction, which allows for amplification of a target sequence using a hybrid RNA/DNA probe and RNase (ID Biomedical); ligase chain reaction (Wu et al. (1989) Genomics vol. 4, pp. 560-569). In a particular embodiment, the chromosomal abnormality associated with a TCL-1 locus can be detected as described in PCT Publication No. WO/92/19775, dated Nov. 12, 1992. In a specific embodiment, the TCL-1 probe used in a hybridization assay is detectably labeled. Such a label can be any known in the art including, but not limited to, radioactive labels, fluorescent labels, biotin, chemiluminescent labels, etc.

In a specific embodiment in which the assay used employs primers, at least one primer can be detectably labeled. In another embodiment, one of a primer pair is attached to a moiety providing for capture, e.g., a magnetic bead.

Anti-TCL-1 antibodies may be generated and used diagnostically to detect the presence of TCL-1 protein product in patient samples thereby identifying disease states associated with chromosome 14 abnormalities. For detection of TCL-1 protein sequences, a diagnostic kit of the present invention comprises, in one or more containers, an anti-TCL-1 antibody which optionally can be detectably labeled. In a different embodiment, the kit can comprise in a container, a labeled specific binding portion of an antibody. As used herein, the term detectable label refers to any label which provides directly or indirectly a detectable signal and includes, for example, enzymes, radiolabelled molecules, fluorescent molecules, particles, chemiluminesors, enzyme substrates or cofactors, enzyme inhibitors, or magnetic particles. Examples of enzymes useful as detectable labels in the present invention include alkaline phosphatase and horse radish peroxidase. A variety of methods are available for linking the detectable labels to proteins of interest, and include for example the use of a bifunctional agent, such as, 4,4'-difluoro-3,3'-dinitro-phenylsulfone, for attaching an enzyme, for example, horse radish peroxidase, to a protein of interest. The attached enzyme is then allowed to react with a substrate yielding a reaction product which is detectable. The present invention provides a method for detecting a TCL-1 protein in a patient sample, comprising, contacting the patient sample with an anti-TCL-1 antibody under conditions such that immunospecific binding can occur, and detecting or measuring the amount of any immunospecific binding by the antibody.

Samples can be any sample from a patient containing TCL-1 protein, e.g., tissue sections, peripheral blood lymphocytes, etc.

In diagnosing disease states, the functional activity of TCL-1 proteins, derivatives and analogs may be assayed by various methods. Accordingly, the present invention also provides a method of diagnosing a T-cell malignancy associated with chromosome 14 abnormalities in a patient comprising, detecting increased expression of TCL-1 protein in a sample from the patient, in which an increase in TCL-1 protein relative to the level found in such an analogous sample from a normal individual, indicates the presence of a T-cell malignancy in the patient.

For example, in one embodiment, where one is detecting or measuring TCL-1 protein by assaying for binding to anti-TCL-1 antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, in situ hybridizations, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention. In particular, such an immunoassay is carried out by a method comprising contacting a sample derived from a patient with an anti-TCL-1 antibody under conditions such that immunospecific binding can occur, and detecting or measuring the amount of any immunospecific binding by the antibody. In a specific embodiment, antibody to a TCL-1 protein can be used to assay a patient tissue or serum sample for the presence of a TCL-1 protein where an increased level of TCL-1 protein is an indication of a diseased condition. In one embodiment of the present invention, the TCL-1 protein is detected or measured by immunocytochemistry of a patient sample. In another embodiment, assays to measure the levels of TCL-1 protein or RNA can be used to moniter therapy of disease associated with increased expression of TCL-1. For example, a decrease in levels of TCL-1 RNA or protein after therapy, relative to the level found before therapy, may be indicative of a favorable response to therapy. An increase in such levels after therapy may be indicative of a poor response to therapy.

In another embodiment, the levels of TCL-1 protein or RNA expression may be used to stage disease, with an increase in TCL-1 protein or RNA expression indicating disease progression.

Other methods will be known to the skilled artisan and are within the scope of the invention.

5.8.2. Therapeutic/Prophylactic Uses

Inhibitors of TCL-1 may be used therapeutically for the treatment of disease states associated with chromosome 14 abnormalities, in particular at 14q32.1, and/or increased expression of TCL-1 protein. In an embodiment of the present invention, a TCL-1 protein and/or cell line that expresses a TCL-1 protein can be used to screen for antibodies, peptides, or other molecules that bind to the TCL-1 protein and thus may act as agonists or antagonists of TCL-1 protein. For example, anti-TCL-1 antibodies capable of neutralizing the activity of a TCL-1 protein may be used to inhibit or prevent a disease state associated with chromosome 14 abnormalities and/or expression of TCL-1 protein, such as T-cell leukemia and lymphoma. Accordingly, the present invention provides a method for treating a disease state associated with a chromosome 14 abnormality in mammal suffering from a disease state associated with a chromosome 14 abnormality comprising, administering a therapeutically effective amount of an anti-TCL-1 antibody to a mammal suffering from a disease state associated with a chromosome 14 abnormality. Alternatively, screening of organic or peptide libraries with recombinantly expressed TCL-1 protein may be useful for identification of therapeutic molecules that function to inhibit the activity of TCL-1 protein. Synthetic and naturally occurring products can be screened in a number of ways deemed routine to those of skill in the art.

The ability of antibodies, peptides or other molecules to modulate the effect of TCL-1 protein on disease states may be monitored. For example, the expression of TCL-1 gene sequences or TCL-1 protein sequences may be detected as described, supra, both before and after administration of a therapeutic composition comprising a TCL-1 nucleotide sequence, TCL-1 protein sequence, derivative or analog thereof, or antibody thereto, of the present invention.

A TCL-1 polynucleotide may be useful in the treatment of various disease states associated with chromosome 14 abnormalities, such as T-cell leukemias and lymphomas, and/or increased expression of TCL-1 protein. By introducing TCL-1 antisense gene sequences into cells, gene therapy can be used to treat conditions associated with over-expression of TCL-1 genes. Accordingly, the present invention provides a method for treating a disease state associated with a chromosome 14 abnormality in mammal suffering from a disease state associated with a chromosome 14 abnormality comprising, administering a therapeutically effective amount of a TCL-1 antisense molecule to a mammal suffering from a disease state associated with a chromosome 14 abnormality.

Oligonucleotide sequences, that include antisense RNA and DNA molecules and ribozymes that function to inhibit the translation of a TCL-1 mRNA are within the scope of the invention. "Antisense" as used herein refers to a nucleic acid capable of hybridizing to a portion of a TCL-1 RNA (preferably mRNA) by virtue of some sequence complementarity. Antisense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of a TCL-1 nucleotide sequence, are preferred. The present invention provides for an antisense molecule comprising a nucleotide sequence complementary to at least a part of the coding sequence of a TCL-1 protein which is hybridizable to a TCL-1 mRNA. The present invention also provides for an antisense molecule comprising a nucleotide sequence complementary to at least a part of the non-coding sequence depicted in FIG. 3B (SEQ ID NO: 3) or FIG. 9 (SEQ ID NO: 5) which hybridizes to said sequence depicted in FIG. 3B (SEQ ID NO: 3) or FIG. 9 (SEQ ID NO: 5), respectively. In a preferred embodiment of the present invention, the antisense gene sequence is derived from the 5' non-coding sequence of a TCL-1 gene. In a particularly preferred embodiment of the present invention, the antisense gene sequence is derived from SEQ ID NO: 3.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of TCL-1 RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

Methods for introducing-nucleic acid into cells or tissue include methods for in vitro introduction of nucleic acid such as the insertion of naked nucleic acid, i.e., by injection into tissue, the introduction of a nucleic acid in a cell ex vivo, the use of a vector such as a virus, retrovirus, phage or plasmic, etc. or techniques such as electroporation which may be used in vivo or ex vivo.

Other methods will be known to the skilled artisan and are within the scope of the invention.

5.9. Demonstration of Therapeutic or Prophylactic Utility

The TCL-1 polynucleotides, TCL-1 protein products, derivatives and analogs thereof, and antibodies thereto, of the invention can be tested in vivo for the desired therapeutic or prophylactic activity. For example, such compounds can be tested in suitable animal model systems prior to testing in humans, including but not limited to rats, mice, chicken, cows, monkeys, rabbits, etc. For in vivo testing, prior to administration-to humans, any animal model system known in the art may be used.

5.9.1. Therapeutic/Prophylactic Methods and Compositions

The invention provides methods of treatment and prophylaxis by administration to a subject of an effective amount of a Therapeutic, i.e., a TCL-1 polynucleotide, TCL-1 protein, derivative or analog thereof, or antibody thereto of the present invention. In a preferred aspect, the Therapeutic is substantially purified. The subject is preferably an animal, including but not limited to animals such as cows, pigs, chickens, etc., and is preferably a mammal, and most preferably human.

Various delivery systems are known and can be used to administer a Therapeutic of the invention, e.g., encapsulation in liposomes, microparticles, microcapsules, expression by recombinant cells, receptor-mediated endocytosis (see, e.g., Wu and Wu, 1987, *J. Biol. Chem.* 262:4429-4432), construction of a therapeutic nucleic acid as part of a retroviral or other vector, etc. Methods of introduction include but are not limited to intradermal, intramuscular, intraperitoneal, intravenous, subcutaneous, intranasal, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In a specific embodiment where the Therapeutic is a nucleic acid encoding a protein therapeutic, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, *Proc. Natl. Acad. Sci. USA* 88:1864-1868), etc. Alternatively, a nucleic acid therapeutic can be introduced intracellularly and incorporated within host cell DNA for expression, by homologous recombination.

The present invention also provides pharmaceutical compositions. Such compositions comprise a therapeutically effective amount of a therapeutic, and a pharmaceutically acceptable carrier or excipient. Such a carrier includes but is not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.9.2. Antisense Regulation of TCL-1 Gene Expression

The present invention provides the therapeutic or prophylactic use of nucleic acids of at least six nucleotides that are antisense to a gene or cDNA encoding TCL-1 or a portion thereof (see also Section 5.8.2). Such antisense nucleic acids have utility as Antagonist Therapeutics of the invention, and can be used in the treatment or prevention of disorders, e.g., T-cell malignancies as described supra in Section 5.8.

The antisense nucleic acids of the invention can be oligonucleotides that are double-stranded or single-stranded, RNA or DNA or a modification or derivative thereof, which can be directly administered to a cell, or which can be produced intracellularly by transcription of exogenous, introduced sequences.

In a specific embodiment, the TCL-1 antisense polynucleotides provided by the instant invention can be used for the treatment of disease states associated with chromosome 14 abnormalities, in particular at 14q32.1, wherein the disease state can be demonstrated (in vitro or in vivo) to express the TCL-1 gene. Such demonstration can be by detection of TCL-1 RNA or of TCL-1 protein.

The invention further provides pharmaceutical compositions comprising an effective amount of the TCL-1 antisense nucleic acids of the invention in a pharmaceutically acceptable carrier, as described supra in Section 5.9.1. Methods for treatment and prevention of disease states associated with chromosome 14, such as T-cell malignancies comprising administering the pharmaceutical compositions of the invention are also provided.

In another embodiment, the invention is directed to methods for inhibiting the expression of a TCL-1 nucleic acid sequence in a prokaryotic or eukaryotic cell comprising providing the cell with an effective amount of a composition comprising an antisense TCL-1 nucleic acid of the invention.

The TCL-1 antisense polynucleotides are of at least six nucleotides and are preferably oligonucleotides (ranging from 6 to about 50 oligonucleotides). In specific aspects, the oligonucleotide is at least 10 nucleotides, at least 20 nucleotides, at least 30 nucleotides, or at least 40 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, *BioTechniques* 6:958-976) or intercalating agents (see, e.g., Zon, 1988, *Pharm. Res.* 5:539-549).

The oligonucleotide may be conjugated to another molecule, e.g., a peptide, hybridization triggered cross-linking agent, transport agent, hybridization-triggered cleavage agent, etc.

Oligonucleotides of the invention may be synthesized by standard methods known in the art, e.g., by use of an automated DNA synthesizer (such as are commercially available from Biosearch, Applied Biosystems, etc.). As examples, phosphorothioate oligos may be synthesized by the method of Stein et al. (1988, *Nucl. Acids Res.* 16:3209), methylphosphonate oligos can be prepared by use of controlled pore glass polymer supports (Sarin et al., 1988, *Proc. Natl. Acad. Sci. USA.* 85:7448-7451), etc.

In a specific embodiment, the TCL-1 antisense oligonucleotide comprises catalytic RNA, or a ribozyme (see, e.g., PCT International Publication WO 90/11364, published Oct. 4, 1990; Sarver et al., 1990, *Science* 247:1222-1225). In another embodiment, the oligonucleotide is a 2'-O-methylribonucleotide (Inoue et al., 1987, *Nucl. Acids Res.* 15:6131-6148), or a chimeric RNA-DNA analogue (Inoue et al., 1987, *FEBS Lett.* 215:327-330).

In an alternative embodiment, the TCL-1 antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the TCL-1 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the TCL-1 antisense RNA can be by any promoter known in the art to act in mammalian, preferably human, cells. Such promoters can be inducible or constitutive. Such promoters include but are not limited to: the SV40 early promoter region (Bernoist and Chambon, 1981, *Nature* 290:304-310), the promoter contained in the 3' long terminal repeat of Rous sarcoma virus (Yamamoto et al., 1980, *Cell* 22:787-797), the herpes thymidine kinase promoter (Wagner et al., 1981, *Proc. Natl. Acad.*

Sci. USA 78:1441-1445), the regulatory sequences of the metallothionein gene (Brinster et al., 1982, Nature 296:39-42), etc.

The antisense nucleic acids of the invention comprise a sequence complementary to at least a portion of an RNA transcript of a TCL-1 gene, preferably a human TCL-1 gene. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded TCL-1 antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a TCL-1 RNA it may contain and still form a stable duplex (or triplex, as the case may be). One skilled in the art can ascertain a tolerable degree of mismatch by use of standard procedures to determine the melting point of the hybridized complex.

The TCL-1 antisense nucleic acids can be used to treat (or prevent) T-cell malignancies, of a cell type which has been shown to express TCL-1 RNA. Malignant, neoplastic, and pre-neoplastic cells which can be tested for such expression include but are not limited to those described supra in Sections 5.8. In a preferred embodiment, a single-stranded DNA antisense TCL-1 oligonucleotide is used.

Malignant (particularly, tumor) cell types which express TCL-1 RNA can be identified by various methods known in the art. Such methods include but are not limited to hybridization with a TCL-1-specific nucleic acid (e.g., by Northern hybridization, dot blot hybridization, in situ hybridization), observing the ability of RNA from the cell type to be translated in vitro into TCL-1, etc. In a preferred aspect, primary tumor tissue from a patient can be assayed for TCL-1 expression prior to treatment.

Pharmaceutical compositions of the invention, comprising an effective amount of a TCL-1 antisense nucleic acid in a pharmaceutically acceptable carrier, can be administered to a patient having a malignancy which is of a type that expresses TCL-1 RNA.

The amount of TCL-1 antisense nucleic acid which will be effective in the treatment of a particular disease state or condition will depend on the nature of the disease state or condition, and can be determined by standard clinical techniques. Where possible, it is desirable to determine the antisense cytotoxicity of the tumor type to be treated in vitro, and then in useful animal model systems prior to testing and use in humans.

In a specific embodiment, pharmaceutical compositions comprising TCL-1 antisense nucleic acids are administered via liposomes, microparticles, or microcapsules. In various embodiments of the invention, it may be useful to use such compositions to achieve sustained release of the TCL-1 antisense nucleic acids. In a specific embodiment, it may be desirable to utilize liposomes targeted via antibodies to specific identifiable tumor antigens (Leonetti et al., 1990, *Proc. Natl. Acad. Sci. USA* 87:2448-2451; Renneisen et al., 1990, *J. Biol. Chem.* 265:16337-16342).

6. Identification of the TCL-1 Gene

This example describes the isolation and characterization of the TCL-1 gene. Two procedures were undertaken in order to isolate the TCL-1 gene. In one procedure, cDNA libraries, constructed from mRNA from an endemic Burkitt lymphoma cell line and two pre-B cell lines, Daudi, 697 and ALL1 were screened using unique probes from the TCL-1 locus on chromosome 14. In the second procedure, exon trapping method (Nehls et al., 1994, *Oncogene* 9(8):2169-2175; Verna et al., 1993, *Nucleic Acids Res.* 21(22):5198:5202; and Auch et al., 1990, *Nucleic Acids Res.* 18(22):6743-6744) using genomic DNA from P1 clones 7-4 and 20-21 was performed.

6.1. Materials and Methods

6.1.1. Isolation of Unique Probes

Unique probes for the isolation of TCL-1 were derived from the human genomic library P1 prepared from human placental DNA (Virgilio et al., 1993, *Proc. Natl. Acad. Sci. USA* 90:9275-9279)). Virgilio et al., identifed P1 library clones 7-4 and 20-21 which were doubly digested, the former with ClaI and EcoRI, and the latter with SalI and EcoRI or with EagI and HindIII, and then subcloned in the vector pBS II available from Stratagene. The subclones were cultured, their DNA was prepared by standard minipreparation method and positive subclones were identified (Sambrook et al., 1989, Molecular Cloning, A Laboratory Manual, 2d ed., Cold Spring Harbor Lab. Press, New York). Repeat free DNA fragments were identified by Southern blot hybridization with human cot-1 DNA (Sambrook et al., 1989, Molecular Cloning, A Laboratory Manual, 2d ed., Cold Spring Harbor Lab. Press, New York).

6.1.2. Exon Trapping

The pE53 vector, a reproduction of the pMHC2 vector (Hamaguchi et al., 1992, *Proc. Natl. Acad. Sci. USA* 89:9779-9783), was provided by Dr. M. Ohta, at the Jefferson Cancer Institute. It contains a portion of p53 exon 10, intron 10, and a portion of exon 11. A unique BglII site is present in intron 10 for cloning. One mg of the DNA of P1 clones 7-4 and 20-21 was partially digested with Sau3A and the digested DNA of molecular weight between 0.5 Kb and 5 Kb was isolated and cloned into the BglII site of pE53. 5 to 10 mg was transfected into semi-confluent COS-7 cells using lipofectase (available from BRL). After 30 hours, total RNA was isolated as described by Buckler et. al. (1991, *Proc. Natl. Acad. Sci. USA* 88:4005-4009). Amplification of total RNA by reverse transcription-PCR was carried out with primers and procedures described by Hamaguchi et. al. (1992, *Proc. Natl. Acad. Sci. USA* 89:9779-9783).

6.1.3. Preparation of cDNA Libraries

A cDNA library from Daudi cell line was constructed with a commercial kit for 1 Zap cDNA synthesis, from Stratagene. The ligation was packaged with Gigapak II Gold packaging extract (Stratagene). cDNA libraries constructed from the cell lines ALL1 and 697 were kindly donated by Dr. T. Nakamura and Dr. A. ar-Rushdi respectively (both at Jefferson Cancer Institute). The libraries were plated and screened using standard protocols (Sambrook et al., 1989, Molecular Cloning, A Laboratory Manual, 2d ed., Cold Spring Harbor Lab. Press, New York).

6.1.4. Prokaryotic Expression

The expression vector pQE30, available from Qiagen, containing the *E. coli* phage T5 promoter, two lac operator sequences and a six histidine affinity tag coding sequences was used for expression of the TCL-1 gene. p697 cDNA was digested with NcoI and EcoRI, and the 5' protruding ends were filled in with the Klenow polymerase (Sambrook et al., 1989, Molecular Cloning, A Laboratory Manual, 2d ed., Cold Spring Harbor Lab. Press, New York). The purified DNA fragment was ligated to pQE30 previously digested with BamHI and treated with Klenow polymerase to blunt the ends. Positives clones were selected and the presence of a continuous open reading frame was confirmed by sequence analysis. Induction of expression of the cloned sequences and purification of the recombinant product was performed according to Qiagen recommendation. A total of 1.5 mg of recombinant product was purified from 400 ml of culture.

6.1.5. In Vitro Translation

The plasmid pALL1 containing full length TCL-1 cDNA was linearized by digestion with ClaI and transcribed and translated in vitro using the TNT Coupled Reticulocyte Lysate system according to manufacturer protocol (Promega). The resulting products were subjected to SDS-PAGE followed by autoradiography.

6.2. Results

6.2.1. Cloning of the TCL-1 Gene

The search for the TCL-1 gene was focused on the region included between the two sets of breakpoints of approximately 160 kb on the TCL-1 locus of chromosome 14 encompassed by the P1 clones 7-4 and 20-21 (Virgilio et al., 1993, Proc. Natl. Acad. Sci. USA 90:9275-9279), as illustrated in FIG. 1. In the effort to identify transcribed sequences, the areas surrounding restriction sites of rare cutter enzymes in these two P1 clones were subcloned and unique probes were isolated. The recognition sites of rare cutter enzymes such as MluI, NruI and NotI, which are rich in CG content, may indicate the existence of a CpG island. Such CpG islands are often found in the proximity of transcribed genes. (Lindsay and Bird, 1987, Nature 327:336-338). Four probes were generated in this way, 7-4CE, 20-7SE, 20-7HE and 9-1KK, whose position is shown in FIG. 1, and hybridized to Northern blots containing RNAs from lymphoid and myelogenous cell lines only the probe 20-7HE and 20-7SE, derived from sequences adjacent to a NotI site (FIG. 1), hybridized with an mRNA from hematopoietic cell lines. This transcript of approximately 1.3 kb in size, was clearly visible in the pre-B acute lymphoblastic leukemia (ALL) cell line ALL380 and in the endemic Burkitt lymphoma cell line Daudi (FIG. 2). Three independent cDNA libraries, constructed from RNA from an endemic Burkitt lymphoma cell line and two pre-B cell lines, Daudi, 697 and ALL1, all of which expressed high levels of the 1.3 kb transcript, were screened with the 20-7HE probe and positive clones were obtained from each library. These clones were designated pA1Daudi, pAl1.5 and p697.

In a parallel effort to identify transcripts, the P1 clones 20-21 and 7-4 were partially digested with Sau3A and cloned into an exon trapping vector containing exon 10, intron 10, and exon 11 of the p53 gene. Several putative exons were isolated, but the majority were due to aberrant splicing at cryptic splicing sites. Some trapped DNA fragments contained Alu repeat sequences and one had high homology to transposon like sequences. However, the sequence of one of the trapped fragments matched the sequence of the cDNA isolated from the 697 and ALL1 libraries and was later found to correspond to exon 3 of the gene.

6.2.2. Sequence Analysis of cDNA Clones

All three cDNA clones, pA1Daudi, pAl1.5 and p697, were entirely sequenced and the complete sequence of pAl1.5 is shown in FIG. 3. Upon sequence comparison, pAl1.5 and p697 cDNAs were found to be identical, except for a base pair substitution at position 404 where a C in pAl1.5 is a T in p697 cDNA. pA1Daudi was incomplete at the 5' end, was missing the first 88 nucleotides, and additionally showed two small internal deletions, the pentamer ATGGT at position 394 and the octamer CTGCCCTT at position 707 (FIG. 3). All three clones of cDNA had 3' untranslated regions of slightly different length. pAl1.5 contained the longest one with the presence of a consensus polyadenylation signal at position 1293.

Sequence analysis of the isolated cDNAs showed the presence of two long open reading frames (ORF). Frame 1 contains an ORF of 342 nucleotides with a starting ATG codon at position 46, located within a perfect Kozak consensus sequence, and with a stop codon at position 388 (FIG. 3). This ORF potentially encodes for a protein of 114 amino acids with a predicted molecular weight of 13.5 kDa. Frame 2 contains an ORF with a starting ATG codon at position 383 and a stop codon at position 773, to give a putative protein of 14.5 kDa in molecular weight. However the presence in this second ORF of a point mutation and a deletion in two of the three independently isolated cDNA clones, as well as the position of this ORF only on the last exon, led us to believe that the second ORF is not translated.

Search of nucleic acid and protein data bases, revealed about a 40% amino acid sequence homology between the TCL-1 protein and the Mature T-Cell Proliferative 1 protein (Stern et al. (1993) Oncogen, vol. 8 pp. 2475-2483) which is involved in a translocation of chromosome 14 and the X chromosome t(14:X) (q11:q28) also found to be associated with T-PLL and AT, see FIG. 8. The GCG Motifs program revealed the existence of a casein kinase II phosphorylation site (MAECPTLGEAVTDH) (a protion of SEQ ID NO:2) starting at amino acid position 6. To confirm the presence of an open reading frame and its ability to encode for a protein, the entire cDNA was subcloned into the prokaryotic expression vector pQE30. FIG. 4 shows the specific induction of a 14 kDa protein and the protein after purification. These results were also confirmed by in vitro translation. In order to study the genomic structure of the gene, a SalI-Hind III fragment, containing the entire cDNA, was subcloned and sequenced. The map and the structure of the gene are shown in FIG. 1. The gene is composed by four small exons with a 3' untranslated region of approximately 800 nucleotides. The sequence immediately 5' to the cDNA showed the presence of five binding sites for the SP1 transcription factor and a TATA box at position −41 (FIG. 3B); these data confirm that the we have isolated a complete cDNA.

6.2.3. Production of Polyclonal Anti-TCL-1 Antibodies

Recombinant TCL-1 protein, expressed in bacteria, was used to immunize rabbits. The antisera raised in the rabbits reacted with a protein of 14 kDa expressed in bacteria containing the recombinant TCL-1 gene, as shown by Western blot. The rabbit anti-TCL-1 antibodies were also able to immunoprecipitate a 14 kDa protein from a variety of leukemic and lymphoid cells expressing TCL-1 mRNA.

7. Expression of the TCL-1 Gene in T-Cell Malignancies

This example illustrates the increased expression of the TCL-1 gene in various T-cell malignancies.

7.1. Materials and Methods

7.1.1. Reverse Transcription-PCR

Amplification of DNA from isolated populations of bone marrow B-cells, T-cell lines, PBL, PHA stimulated PBL and thymus was performed using reverse transcriptase PCR. First strand DNA synthesis was performed using 1 mg of total RNA with either M-MLV (available from BRL) or AMV or Superscript (available from BRL) reverse transcriptase and respective reaction buffer with either oligo dT or random primers. One tenth of the reaction was subsequently used for each single PCR amplification. Amplification of DNA from isolated populations of bone marrow B-cells, T-cell lines, PBL, PHA stimulated PBL and thymus was carried out with TCL-1 primers p9A-TGCTGCCAGATGACTGATGT (SEQ ID NO: 6) and Rev III CAAATGGAATCCTCCTTGGC, (SEQ ID NO: 7) under the following conditions. The nucleic acid was denaturing for 1 min. at 94° C., then allowed to anneal for 1 min. at 58° C., then allowed to elongate for 1 min. at 72° C. for a total of 30 cycles. Amplification of DNA from patients with T-PLL was carried out with TCL-1 primers Daudi uni1-AGGCCTATGACCCCCACC (SEQ ID NO: 8) and Daudi rev2-CATTCCTCCCAGACCCCA, (SEQ ID NO: 9) under the same conditions as above, except for the annealing temperature which was 60° C. As PCR internal standard, primers specific for the B-actin gene were used: A1-TCAT-CACCATTGGCAATGAG (SEQ ID NO: 10) and A2-CAGT-GTGTTGGCGTACAGGT (SEQ ID NO: 11). These primers were used under the same conditions as the TCL-1 primers.

7.1.2. Isolation of Lymphocyte Cells by Immunofluorescence Cell-Sorting

Bone marrow cells were obtained from 18-22 week fetal material, in accordance with policies established by an institutional review board. Mononuclear bone marrow cells were then isolated by centrifugation of cell suspensions over a Ficoll-Hypaque gradient (Nishimoto et al., 1991, Proc. Natl. Acad. Sci. USA 88:6284-6288). The monoclonal antibodies (MAbs) used for cell surface analysis included anti-human Leu-12, which recognizes the pan-B cell antigen CD19, anti-human HPCA-2, which detects the early stem cell marker CD34 (Becton-Dickinson), and goat-anti-human IgM (Southern Biotechnology Associates). For two-color surface analysis for cell-sorting, viable FBM cells were incubated with fluorescein isothiocyanate (FITC)-conjugated anti CD34 antibodies or goat-anti-hu IgM for 15 minutes on ice, washed with PBS containing 2% HIFCS, and counterstained with phycoerythrin (PE)-conjugated MAb specific for CD19. Subpopulations of lymphocytes were sorted according to immunofluorescence and light scatter characteristics with a FACS-Star instrument (Becton-Dickinson). The lymphocyte subpopulations collected were CD34+CD19−, CD34+ CD19+, CD19lom−, CD19hi m−, CD19+mlo, and CD19+ mhi. Cells were collected, counted, and total RNA was extracted using Tri-Reagent (Molecular Research Center). RNA was subjected to Northern blot analysis to reveal the existence a TCL-1 transcript.

7.1.3. Cell Lines and Lymphocytes

A variety of human cell lines derived from T-cell leukemias were subjected to Northern blot analysis to detect the existence of a TCL-1 transcript. The majority of the cell lines were obtained from American Type Culture Collection (ATCC). SupT11, is a cell line derived from patient NL (Smith et al., 1989, Blood 73:2182-2187). Peripheral lymphocytes were isolated from whole blood by centrifugation on a Ficoll-Hypaque gradient, followed by a one hour adherence in petri dishes to remove the monocytes. Stimulation with phytohemagglutinin (PHA) was carried at a final concentration of 0.1% for 3 days. Patients 62 and 312, presented with T-PLL involving an inversion of chromosome 14, inv(14) (q11; q32.1). In order to determine if the isolated gene is deregulated in cells with the t(14:14) (q11:q32) translocation, we carried out Northern blot analysis comparing the amount of TCL-1 transcript present in resting peripheral blood lymphocytes (PBL), PHA activated PBL, SupT11 cells, a cell line established from a patient with T-ALL with a t(14:14) chromosomal translocation (Lindsay and Bird, 1987, Nature 327: 336-338; Bertness et al., 1990, Cancer Genet. Cytogenet. 44:47-54), and in a variety of human cell lines derived from T-cell leukemias (Table 1).

We detected high levels of expression in SupT11 cells (FIG. 5A). No expression was detectable in several other tumor derived T-cell lines lacking the TCL-1 translocation, such as Molt 4, HUT78, Jurkat and SupT1 (FIG. 5B) (Table 1). These results were also confirmed by the sensitive assay of RT-PCR as shown in FIG. 5C. Of interest is the fact that SupT1 cells carry an inverted chromosome 14, inv 14 (q11; q32), in which the TCRα locus is not juxtaposed to the TCL-1, but is positioned in front of the immunoglobulin heavy chain locus at 14q32.3 (Baer et al., 1985, Cell 43:705-713). SupT1 cells also carry a translocation between chromosome 7 and 9, that juxtaposes the TCRβ locus to the TAN-1 oncogene (Ellisen et al., 1991, Cell 66:649-661). Thus an inversion of chromosome 14 that does not involve the TCL-1 locus is unable to deregulate the TCL-1 gene. Furthermore we performed a semiquantitative RT-PCR analysis on two independent cases of T-PLL carrying an inversion of chromosome 14, inv(14) (q11;q32). Both cases showed high expression levels of the TCL-1 gene, comparable to those observed in the SupT11 cell line (FIG. 6).

7.2. Results 7.2.1. Characterization of the TCL-1 Gene

The TCL-1 gene is located in a chromosomal region banded by two clusters of breakpoints. In its strategic position, between the two clusters of breakpoints, the TCL-i gene becomes juxtaposed to TCR-Cα/δ regulatory elements in both types of rearrangements involving 14q32.1. In the case of inversions the TCL-1 gene is telomeric to the 14q32.1 break, hence the central part of the chromosome between q11 and q32 has flipped upside down and Cα/δ has been positioned centromeric and in proximity to the TCL-1 gene, the same holds true for translocations with inverted duplication. In the case of simple translocations, the gene is centromeric to the breaks and does not move during the rearrangement. In this case the break on the other chromosome 14 occurs in TCR α/δ locus that moves to a region telomeric to the TCL-1 gene. In this model of activation the TCL-1 gene is activated by the control elements of the TCR gene, whether they are positioned 5' of the TCL-1 gene, as in the cases of translocations, or 3' to TCL-1, as in the cases of inversions. A similar situation has been observed in Burkitt's lymphomas, where the Ig enhancers can be located upstream to the MYC oncogene in lymphomas with the t(8;14) chromosomal translocation (Dalla-Favera et al., 1982, Proc. Natl. Acad. Sci. USA 79:7824-7827; Erikson et al., 1986, Science 232:884-886) or downstream to MYC in lymphomas with the t(8;22) or the t(2;8) chromosomal translocation (Croce et al., 1983, Proc. Natl. Acad. Sci. USA 80:6922-6926; Erikson et al., 1983, Proc. Natl. Acad. Sci. USA 80:7581-7585). Similarly Ig enhancers are found downstream to the BCL-2 gene in follicular lymphomas (Tsujimoto et al., 1985, Science 228:1440-1443; Tsujimoto and Croce, 1986, Proc. Natl. Acad. Sci. USA 83:5214-5218) and upstream to the BCL-2 gene in B-cell chronic lymphocytic leukemia (Adachi et al., 1989, Proc. Natl. Acad. Sci. USA 86:2771-2774).

7.2.2. Expression of the TCL-1 Gene in Tumors and Normal Human Tissues

A large number of RNAs from tumor cell lines, both of lymphoid and non-lymphoid origin, were screened to study the pattern of expression of the TCL-1 gene. The results summarized in Table 1 reveal that the TCL-1 gene is expressed at high levels in pre-B cells and in endemic Burkitt's lymphoma cells, which express cell surface IgM and do not secrete Ig (Magrath et al., 1980, J. Natl. Cancer Inst. 64:477-483), but is not expressed in sporadic Burkitt's lymphomas which secrete Ig. This data is illustrated by the presence of TCL-1 transcripts in 697, ALL-1 and BV173 cell lines, all with a pre-B cell phenotype and by its absence in B-lymphoblastoid cell lines such as GM1500 and RPMI 8866. Expression of the TCL-1 gene, at different stages of normal B cell differentiation, was studied by RT-PCR. Fetal bone marrow B-cell subpopulations were isolated by FACS, cDNAs prepared and PCR carried out with a primer from exon 3, p9A, and one from the 3' untranslated region, RevIII, to give a fragment of 270 bp. The results are shown in FIG. 6. No signal is present in the CD34+ CD19− stem cell rich fraction. Weak expression appears in CD34+ CD19+ subpopulation of pro B cells, and expression peaks in IgM− pre B cells expressing high levels of CD19. The levels of expression remain high in immature IgM+ B cells (FIG. 7) in the fetal bone marrow, whereas the signal is not detectable in mature peripheral B lymphocytes (FIG. 5). No expression of TCL-1 was observed in myelogenous cell lines or in cell lines derived from gastric, mammary or prostate carcinomas (Table 1). Furthermore no expression of this gene was observed in polyadenylated RNA isolated from a variety of normal human tissues such as heart, brain, placenta, lung, liver, skeletal muscle, kidney and pancreas (Northern blots obtained from Clontech). The results, taken together, suggest that TCL-1 is expressed specifically in lymphoid cells.

The results suggest that TCL-1 expression begins in normal B lineage cells as early as the CD34+CD19+ pro B cell stage. Its expression peaks in pre B cells, which express high levels of CD19 but no cell surface IgM, and its expression remains high in immature IgM+ cells in the bone marrow. A similar pattern of TCL-1 expression is noted for T lineage cells. Immature thymocytes, including the intermediate CD4+/CD8+ population express TCL-1 transcripts, whereas mature T cells in circulation do not, unless they are activated, when low levels of TCL-1 transcripts may be expressed. In contrast mature B cells in the periphery do not express TCL-1. These findings parallel the results obtained with the lymphoid cell lines where pro B cell lines with the t(4;11) chromosome translocation failed to express TCL-1, while high levels of TCL-1 transcripts were detected in pre B cell lines. This suggests that expression of TCL-1 may be linked to immunoglobulin and T cell receptor gene rearrangement and expression. The high level of expression of TCL-1 in leukemic T cells with the t(14:14) translocation and the inv(14) inversion, but not in leukemic T cell lines with other types of chromosomal rearrangements, strongly supports the conclusion that this gene becomes deregulated as a consequence of its juxtaposition to the α/δ locus of the T cell receptor.

TABLE 1

EXPRESSION OF TCL-1 mRNA IN CELL LINE

| Cell Line | Tumor | Translocation | RNA |
|---|---|---|---|
| U266* | ALL | t(4; 11) | – |
| RS(4; 11)* | " | t(4; 11) | – |
| MV(4; 11) | " | t(4; 11) | – |
| B1 | " | t(4; 11) | – |
| ALL380 | " | t(8; 14), t(14; 18) | + |
| ALL-1 | " | t(9; 22) | + |
| BV173 | " | t(9; 22) | + |
| RPMI 8866 | B-lymphoblastoid | N/A | – |
| GM1500 | " | Normal | – |
| RPMI 8226 | Myeloma | Multiple Rearrangements | – |
| P3HR-1* | Endemic Burkitt | t(8; 14) | + |
| AKUA | " | t(8; 14) | + |
| Daudi* | " | t(8; 14) | + |
| SKDHL | Sporadic Burkitt | t(8; 14) | – |
| BL 2 | " | t(8; 22) | – |
| RS 11846 | High grade B-cell lymphoma | t(14; 18, t(8; 22) | + |
| K562 | CML | t(9; 22) | – |
| PEER | T-ALL | Multiple Rearrangements | – |
| Jurkat* | " | Multiple Rearrangements | – |
| Molt 4* | " | t(7; 7), 6q- | – |
| CEM* | " | Multiple Rearrangements | – |
| Sup T1 | " | inv(14) (q11; q32.3) | – |
| Sup T11 | " | t(14; 14) (q11; 32.1) | + |
| HUT 78 | T-Sezary Syndrome | N/A | – |
| HL60* | AML | Multiple Rearrangements | – |
| KG-la* | " | Multiple Rearrangements | – |
| U937* | Histiocytic Lymphoma | Multiple Rearrangements | – |
| I32 | Retinoblastoma | Multiple Rearrangements | – |
| MGC | Gastric Carcinoma | Multiple Rearrangements | – |
| KATO* | " | Multiple Rearrangements | – |
| SW 48* | Colorectal Carcinoma | Multiple Rearrangements | – |
| LNCap* | Prostrate Carcinoma | Multiple Rearrangements | – |
| PC3 | " | Multiple Rearrangements | – |
| T98G* | Glioblastoma | Multiple Rearrangements | – |

N/A = not done
The cell lines with multiple rearrangements do not have translocations or rearrangements at 14q32.1.
*ATCC available

9. Deposit of Microorganisms

Plasmid pAl1.5, containing a full-length TCL-1 cDNA as an EcoRI insert into the pBluescript SK+ vector (Stratagene); and plasmid p20-7SE, containing a genomic sequence of TCL-1 (including the 5' sequence shown in FIG. 3B) as a SalI-EcoRI insert into the pBluescript SK+ vector; were both deposited on Oct. 25, 1994, with the American Type Culture Collection, 1201 Parklawn Drive, Rockville, Md. 20852, under the provisions of the Budapest Treaty on the International Recognition of the Deposit of Microorganisms for the Purposes of Patent Procedures.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method for detecting a TCL-1 protein in a patient sample, comprising:
   (a) contacting the patient sample with an antibody that binds to an epitope of a TCL-1 protein, under conditions such that immunospecific binding can occur, and
   (b) detecting or measuring the amount of any immunospecific binding by the antibody.

2. The method of claim 1, wherein the TCL-1 protein is a human protein.

3. The method of claim 1, wherein said immunospecific binding by the antibody is assayed using a Western blot.

4. The method of claim 1, wherein said immunospecific binding by the antibody is assayed using an enzyme linked immunosorbent assay (ELISA), an in situ hybridization assay or an immunoprecipitation.

5. The method of claim 1, wherein the antibody is selected from the group consisting of a polyclonal antibody, a monoclonal antibody, a chimeric antibody, a single chain antibody, a human antibody, and an antibody fragment.

6. The method of claim 1, wherein the antibody is an antibody fragment selected from the group consisting of an Fab fragment, an Fab' fragment and an F(ab')$_2$ fragment.

7. The method of claim 1, wherein the immunospecific binding by the antibody is detected or measured using an assay selected from the group consisting of a radioimmunoassay, an enzyme linked immunosorbent assay (ELISA), a sandwich immunoassay, an immunoradiometric assay, a gel diffusion precipitin reaction, an immunodiffusion assay, an in situ immunoassay, a western blot, an in situ hybridization, a precipitation reaction, an agglutination assay, complement fixation analysis, an immunofluorescence assay, a protein A assay, and an immunoelectrophoresis assay.

8. The method of claim 1, wherein the immunospecific binding by the antibody is detected by immunocytochemistry of a patient sample.

\* \* \* \* \*

SEQUENCE LISTING

<160> NUMBER OF SEQ ID NOS: 12

<210> SEQ ID NO 1
<211> LENGTH: 1324
<212> TYPE: DNA
<213> ORGANISM: Artificial Sequence
<220> FEATURE:
<223> OTHER INFORMATION: Description of Artificial Sequence: cDNA
      sequence of TCL-1

<220> FEATURE:
<221> NAME/KEY: CDS
<222> LOCATION: (49)..(387)

<400> SEQUENCE: 1

```
cttgagaggc tctggctctt gcttcttagg cggcccgagg acgccatg gcc gag tgc        57
                                                    Ala Glu Cys
                                                     1 ccg aca ctc ggg gag gca gtc acc gac cac ccg gac cgc ctg tgg gcc        105
Pro Thr Leu Gly Glu Ala Val Thr Asp His Pro Asp Arg Leu Trp Ala
  5                  10                  15 tgg gag aag ttc gtg tat ttg gac gag aag cag cac gcc tgg ctg ccc        153
Trp Glu Lys Phe Val Tyr Leu Asp Glu Lys Gln His Ala Trp Leu Pro
 20                  25                  30                  35 tta acc atc gag ata aag gat agg tta cag tta cgg gtg ctc ttg cgt        201
Leu Thr Ile Glu Ile Lys Asp Arg Leu Gln Leu Arg Val Leu Leu Arg
                 40                  45                  50 cgg gaa gac gtc gtc ctg ggg agg cct atg acc ccc acc cag ata ggc        249
Arg Glu Asp Val Val Leu Gly Arg Pro Met Thr Pro Thr Gln Ile Gly
             55                  60                  65 cca agc ctg ctg cct atc atg tgg cag ctc tac cct gat gga cga tac        297
Pro Ser Leu Leu Pro Ile Met Trp Gln Leu Tyr Pro Asp Gly Arg Tyr
         70                  75                  80 cga tcc tca gac tcc agt ttc tgg cgc tta gtg tac cac atc aag att        345
Arg Ser Ser Asp Ser Ser Phe Trp Arg Leu Val Tyr His Ile Lys Ile
     85                  90                  95 gac ggc gtg gag gac atg ctt ctc gag ctg ctg cca gat gac                387
Asp Gly Val Glu Asp Met Leu Leu Glu Leu Leu Pro Asp Asp
100                 105                 110 tgatgtatgg tcttggcagc acctgtctcc tttcacccca gggcctgagc ctggccagcc      447
tacaatgggg atgttgtgtt tctgttcacc ttcgtttact atgcctgtgt cttctccacc      507
acgctggggt ctgggaggaa tggacagaca gaggatgagc tctacccagg gcctgcagga      567
cctgcctgta gcccactctg ctcgccttag cactaccact cctgccaagg aggattccat      627
ttggcagagc ttcttccagg tgcccagcta tacctgtgcc tcggcttttc tcagctggat      687
gatggtcttc agcctctttc tgtcccttct gtccctcaca gcactagtat ttcatgttgc      747
acacccactc agctccgtga acttgtgaga cacagccga ttcacctgag caggacctct       807
gaaaccctgg accagtggtc tcacatggtg ctacgcctgc atgtaaacac gcctgcaaac      867
gctgcctgcc ggtaaacacg cctgcaaacg ctgcctgccc gtaaacacg ctgcaaacgc       927
tgcctgccca cacaggttca cgtgcagctc aaggaaaggc ctgaaaggag cccttatctg      987
tgctcaggac tcagaagcct ctgggtcagt ggtccacatc ccgggacgca gcaggaggcc     1047
aggccggcga gccctgtgga tgagccctca gaacccttgg cttgcccacg tggaaaaggg     1107
atagaggttg ggtttccccc ctttatagat ggtcacgcac ctgggtgtta caaagttgta     1167
tgtggcatga atacttttttg taatgattga ttaaatgcaa gatagtttat ctaacttcgt     1227
gcgcaatcag cttctatcct tgacttagat tctggtggag agaagtgaga ataggcagcc     1287
cccaaataaa aaatattcat ggaaaaaaaa aaaaaa                               1324
```

<210> SEQ ID NO 2
<211> LENGTH: 113
<212> TYPE: PRT
<213> ORGANISM: Artificial Sequence
<220> FEATURE:
<223> OTHER INFORMATION: Description of Artificial Sequence: cDNA sequence of TCL-1

-continued

```
<400> SEQUENCE: 2

Ala Glu Cys Pro Thr Leu Gly Glu Ala Val Thr Asp His Pro Asp Arg
1               5                   10                  15

Leu Trp Ala Trp Glu Lys Phe Val Tyr Leu Asp Glu Lys Gln His Ala
            20                  25                  30

Trp Leu Pro Leu Thr Ile Glu Ile Lys Asp Arg Leu Gln Leu Arg Val
        35                  40                  45

Leu Leu Arg Arg Glu Asp Val Val Leu Gly Arg Pro Met Thr Pro Thr
    50                  55                  60

Gln Ile Gly Pro Ser Leu Leu Pro Ile Met Trp Gln Leu Tyr Pro Asp
65                  70                  75                  80

Gly Arg Tyr Arg Ser Ser Asp Ser Ser Phe Trp Arg Leu Val Tyr His
                85                  90                  95

Ile Lys Ile Asp Gly Val Glu Asp Met Leu Leu Glu Leu Leu Pro Asp
            100                 105                 110

Asp

<210> SEQ ID NO 3
<211> LENGTH: 560
<212> TYPE: DNA
<213> ORGANISM: Artificial Sequence
<220> FEATURE:
<223> OTHER INFORMATION: Description of Artificial Sequence: genomic
      sequence of  TCL-1

<400> SEQUENCE: 3
gtcgactgtg agttcccagc agaggcccag agtcccggtc cggcagccga gggaagcggg     60
ggggtcttcc agaagaagaa agggccaagg tcaccccggt gcctctccag cagcagcaga   120
gggcggcggt cggtgtcgct gctggccggg gcctcgagga aggcgcgggc cagctggggc   180
cgggtctgcg ttcccaggag ctgccaccgt tccaggagc aagtcaggcc gggacgttag    240
cgcctgcgcg ggaccctcac ttgccaccaa gaccccaca aaccccgccc catccttagc    300
gcctgcgcgg gaccctcact tgccaccaag accccacaa accccgcccc atcctgcctt    360
acgccccgcc ccaaggtcgt tctcccgacc cggggtcccg cccaagacc gtcctcccgc    420 cccgccgctt ggtggcggcc gcatgctgcc cggatataaa gggtcggccc cacatcccag   480
ggaccagcga gcggccttga gaggctctgg ctcttgcttc ttaggcggcc cgaggacgcc   540
atggccgagt gcccgacact                                                560

<210> SEQ ID NO 4
<211> LENGTH: 108
<212> TYPE: PRT
<213> ORGANISM: Artificial Sequence
<220> FEATURE:
<223> OTHER INFORMATION: Description of Artificial Sequence: MTCP1
      protein
<220> FEATURE:
<221> NAME/KEY: SITE
<222> LOCATION: 108
<223> OTHER INFORMATION: Xaa = any amino acid

<400> SEQUENCE: 4

Met Ala Gly Glu Asp Val Gly Ala Pro Pro Asp His Leu Trp Val His
1               5                   10                  15

Gln Glu Gly Ile Tyr Arg Asp Glu Tyr Gln Arg Thr Trp Val Ala Val
            20                  25                  30

Val Glu Glu Glu Thr Ser Phe Leu Arg Ala Arg Val Gln Gln Ile Gln
        35                  40                  45
```

-continued

```
Val Pro Leu Gly Asp Ala Ala Arg Pro Ser His Leu Leu Thr Ser Gln
        50                  55                  60

Leu Pro Leu Met Trp Gln Leu Tyr Pro Glu Glu Arg Tyr Met Asp Asn
 65                  70                  75                  80

Asn Ser Arg Leu Trp Gln Ile Gln His His Leu Met Val Arg Gly Val
                 85                  90                  95

Gln Glu Leu Leu Leu Lys Leu Leu Pro Asp Asp Xaa
            100                 105
```

<210> SEQ ID NO 5
<211> LENGTH: 4922
<212> TYPE: DNA
<213> ORGANISM: Artificial Sequence
<220> FEATURE:
<223> OTHER INFORMATION: Description of Artificial Sequence: genomic
      DNA of TCL-1
<220> FEATURE:
<221> NAME/KEY: mod_base
<222> LOCATION: 373, 688, 1155, 1214, 1283, 1334, 1335, 2153, 2180,
      2201, 2224, 2225, 2279, 2501, 2523, 2545, 2553, 2566, 2592, 2599,
      3955, 3959, 3975, 3976, 3982, 3984, 3987, 3990, 3992, 4001, 4027,
      4029, 4072, 4194, 4372, 4539, 4543, 4584, 4610, 4620, 4626, 4632,
      4641, 4657, 4669, 4673, 4674, 4686, 4688, 4690, 4691, 4698, 4709,
      4715, 4734, 4736, 4746, 4755, 4777, 4778, 4783, 4784, 4789, 4792,
      4804, 4812, 4814, 4824, 4825, 4830, 4835, 4840, 4841, 4851, 4856,
      4858, 4862, 4869, 4890, 4891, 4897, 4901, 4903, 4906, 4914
<223> OTHER INFORMATION: n = a, t, g or c

<400> SEQUENCE: 5

```
gtcgacttgt gaktyccmag magaggccca gaagtcccgg tccggcaaag cggaggggaa      60
gcgggggggg tcttccaaga agaagaaagg gcccaaggtt caaccccgg tgccttctcc      120 agcagcaagc aagagggcgg cgggtcggtt gtcgctgctg gccggggccc tccgaggaaa     180
ggcgcggrcc agctggggcc gggtctgcgt tcccaggagc tgccaccgtt ccagggagca     240
agtcaggccg ggacgttagc gcctgcgcgg gaccctcact tgccaccaag rmccccacaa     300
accccgcccc atcctgyctt acgccccgcc ccaaggtcgg ttctccccga cccggggtc      360 ccgcccccaa ggnccgtcct ccccgccccc gccgsttggt ggcggccgca tgctgcccgg     420
atataaaggg tcggccccac atcccaggga ccagcgagcg gccttgagag gctctggctc     480
ttgcttctta ggcggcccga ggacgccatg gccgagtgcc cgacactcgg ggaggcagtc     540
accgaccacc cggaccgcct gtgggcctgg agaagttcg tgtatttgga cgagaagcag      600
macgcctgcc tgcccttaac catcgaggta caaccaccttt ggagcggat ggcgargcag     660 caggggcasc ccctgggagc ttgggatncc ctaggaaggg cgaggactca aggagcactc     720 actatgggc agggaggatc ccccacagat kaagccactt ttggagccgg sctctkgagg     780
gatgaatagg agttcctcca ggcagggaag aagggtggga aaaccccaaa ggaatgtcgg     840
tcaaaggggt ggacccagtg cctgtggagt gtgactataa tgttgactac agcaggcatt     900 ttctggctt cggggtccta atccttaaaa atgggtatct ctaagtgact catccatatg      960
gccgattatc ggaatcatct caggtgggtc ccagaaatct gtatttttaa aaagaacccw    1020
cmacagttta gggtccaacc caggcataac caaaacactg gcctaagagt tgtgaagtat    1080
tttcccacct accctctggg ctttatttaa gamaaccaaa tttaacaagt gatgtcgtag    1140
tataagcgcc ggtantkgaa ycaatattga cttttttaat gtgtgatgcc ttaagatggg    1200
tccttaatcc atgttaagnt tttgttaaag aaatagataa gtcttttaca agtatttgga    1260
tttactcaat gaaaagagt canaaaatgt tcaaactctc tccaaacata cactgaagaa     1320
agcataaaaa ttannaaata tattagaaca cgtatgtcca gtagcaawca maaattattg    1380
```

```
agtgttgayt gtgtctctac agatgggaaa ctgaggcaca cmaaatgtac atttgtccga      1440
ggtaagattg ctagtaggta atggggttgg aattctaggc tcttaaccac cacaaaatct      1500
gcatttttat tggcatttca attttttaaa tatgttttta ctttaaaaat caagttaaat      1560
acttactttt ttaaaatcaa aatttgaaga ataatttga agattcagtg gatttctttt        1620
tttaaatctc tgagaaatct cttccctyca acgtgacacc maaaccmgcg aaccagacag       1680
ttttttcataa aatcatgaaa catgcyccmc maaaaataac ccactascaa actgtgggac     1740
agattttgcc tcacatcatt gaaaaggcca gcawtctttt tctctctttc tttctttgkt      1800
gttttttttt tttcctgtag awacagggtc tcgctctgtg acccaggctg gtctyaaact      1860
cctggcctca agcgatcctc ctgcctctgc cttccaaagc actggaatta caagtgtgag      1920
ccgctgcaac ccgccagaaa aaagtgtgcc tttcatggcc ctgtctgggt ggctagacac      1980
gtgtgtgtgc tggtggtcct ggcccagcca gagttccctg agaggagcat gcatggccta      2040
aggaagtgag cttcagggaa cagtgatgac catcatttca cactcggacc ccctgccmaa      2100
gatgggtgga tgsctgscag ggagggattc cggtkttcct gcgcctggag aancccctgcc    2160
aagcggaacc tgaaagtatn ccctgtcctt ttcttctcct nagataaagg ataggttaca      2220
gttnngggtg ctcttgcgtc gggaagacgt cgtcctgggg aggcctatga cccccaccna     2280
gataggccca agcctgctgc ctatcatgtg gcagctctac cctgatggac gataccgatc      2340
ctcagactcc agtttctggc gcttagtgta ccacatcaag gtgagtgtct ttctcccaga      2400
ggtccatcgg ktgatcttgg gtttcccctc cycmatgtct gscttagtg gtttaycttc       2460
ccyccatccc agtssgcaaa agcattwaaa aratgggga nrtrwacmas tgcagatttc       2520
tanaggactt taccagagag aaganagatc ctntgaggtc tctaanagaa ccctacctcc     2580
acttcctccc anccaccanc taaccgcagg aagacatctc tggtggggmm kcacaggctg     2640
aaggctggtg ggaggagggr caktctccaa gasccccctga aatcctcaca cctgggttcc   2700
tacctgctgt ttccagctag gggaagscsc aggagtgagg aatggaggga gtggagggct    2760
ctggccgatc aatgccttct ctctctctct gcctctcaga ttgacggcgt ggaggacatg      2820
cttctcgagc tgctgccaga tgactgatgt atggtgagct ccactggagc ctgacccctc      2880
ttagtccaca gtggctgtat cagaaagaaa gaccacccct tctccatgaa ggcagtgcta      2940
acccctcccc gactgctgcc atctgagggt ccctagggat gggagaggct tcctggaggc      3000
actcatgtct cccttaccac ttcgggagcc aagggctttg gtaggcagcc ccctttatcg     3060
cagctgctca tatctataaa gtacttcaca agtttcagct ggcactttca ttttaccatt     3120
gcttttttt tctttgggag atgagtctgg ctctgtggcc caggctagag tgtagtgggt      3180
gcaatctcag ctcactgaaa gctctgcctc ccgggttcac accattctcc tgcctcagcc    3240
ctcggagtag ctgggactac aggcgcccgc caccacacct ggctaatttt tttttttttw   3300
ttwtwttttt tagtagagmc gggtttcac cgtgttagcc aggatggtct cgatctcctg     3360
acctcatgat ctgcccgcct cggcctccca aagtgctggg attacaggca tgagccacca   3420
cgtccggcct taccattgct ttattaaata agcactggtg cttgattata tcagctgagc    3480
cagatattag atacgctatt gagttttgrg gaaataagag taccaaaact cagaaatgag    3540
ttgaagtata gtgacatctt cagattacag acccaggtgt cagaatttgc cttggctcag    3600
aaggcctctg ggggccatcc ctgaccacta ggcttcccac ttagacctgc tccagcagca   3660
ccacccctcg scactgcctg gtccttttcct tcacccttga ttctgtcttc ttttgtcctt     3720
ctccaggtct tggyagcacc tgtctccttt caccccaggg cctgagcctg gccagcctac    3780
```

-continued

```
aatgggatg ttgtgtttct gttcaccttc gtttactatg bctgtgtctt ctccaccacg    3840
ctggggtctg ggaggaatgg acagacagag gatgagctct acccrgggcc tgsaggacct   3900
gtcctgtagm ccactctgct cgccttagsa cctacsactc cwrccgasga ggatnccant   3960
tggaagagct tcttnnaggt gncnaanaan anctgtgcgt nggcttttct cagctggatg   4020
atggtcntna gcctctttct gtcccttctg tccctcacag cactagtatt tnatgttgca   4080
cacccactca gctccgtgaa tttgtgagaa cacaaccgat tcacctgagc aggacctctg   4140
aaaccctgga ccagtggtct cacatggtgc tacgcctgca tgtaaacacg cctncaaacg   4200
ctgcctgcck gtraacacgm sksyrmacag stgmswrccc gtaaacacgc ctgcaaacgc   4260
tgcctgccca cacaggttca cgtgcagctc aaggaaagrm ctgaaarrag cccttatctg   4320
tgctcaggac tcagaagcct ctgggtcagt ggtccacatc ccgggacgca gnaggaggcc   4380
aggccggcga gcctgtgga tgagccctca gaaccttgg gttgcccacg tggaaaaggg     4440
atagaggttg ggtttccccc cttttataga tggtcacgca cctgggtgtt acaaagttgt   4500
atgtggcatg aatacttgnt gtnatgattg attaaatgca agatagttta tctaacttcg   4560
tgcggaatca gcttctatcc ttgncttaga ttctggtgga gagaagtgan aataggcagn   4620
ccccanataa anaatattca ngggatttat tttattnttc cttttgggng atnngggact   4680
acattntncn nccccgtnta atccaatgnt taaancccca gtgttcttgg aggncntacg   4740
tcgaanacca ttggngtang caacctcaaa atttttnngt tgnnaattnc cngttttcca   4800
gagncccccc cntnctccat cttnntcctn gcccncccctn ncctcccnca ntcccnangt  4860 tncccctcgnc cccagtcagt tctttctccn nctttanccg ntnatntcac cagnttcttt  4920
ct                                                                  4922
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: p9A primer

<400> SEQUENCE: 6
tgctgccaga tgactgatgt                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Rev III
      primer

<400> SEQUENCE: 7
caaatggaat cctccttggc                                               20

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Daudi unil-
      primer -continued

```
<400> SEQUENCE: 8
aggcctatga cccccacc                                                     18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Daudi rev2
      primer

<400> SEQUENCE: 9
cattcctccc agacccca                                                     18

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: A1 primer

<400> SEQUENCE: 10
tcatcaccat tggcaatgag                                                   20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: A2 primer

<400> SEQUENCE: 11
cagtgtgttg gcgtacaggt                                                   20

<210> SEQ ID NO 12
<211> LENGTH: 113
<212> TYPE: PRT
<213> ORGANISM: Artificial Sequence
<220> FEATURE:
<223> OTHER INFORMATION: Description of Artificial Sequence: TCL-1
      protein
<220> FEATURE:
<221> NAME/KEY: SITE
<222> LOCATION: 113
<223> OTHER INFORMATION: Xaa = any amino acid

<400> SEQUENCE: 12

Met Ala Glu Cys Pro Thr Leu Gly Glu Ala Val Thr Asp His Pro Asp
 1               5                  10                  15

Arg Leu Trp Ala Trp Glu Lys Val Tyr Leu Asp Glu Lys Gln His Ala
                20                  25                  30

Trp Leu Pro Leu Thr Ile Glu Ile Lys Asp Arg Leu Gln Leu Arg Val
            35                  40                  45

Leu Leu Arg Arg Glu Asp Val Val Leu Arg Ser Met Thr Pro Thr Gln
        50                  55                  60

Ile Gly Pro Ser Leu Leu Pro Ile Met Trp Gln Leu Tyr Pro Asp Gly
65                  70                  75                  80

Arg Tyr Arg Ser Ser Asp Ser Ser Phe Trp Arg Leu Val Tyr His Ile
                85                  90                  95

Lys Ile Asp Gly Val Glu Asp Met Leu Leu Glu Leu Leu Pro Asp Asp
               100                 105                 110

Xaa
```